United States Patent [19]

Pittet et al.

[11] 4,316,995
[45] Feb. 23, 1982

[54] PROCESS FOR PREPARING VINYL PHENOL

[75] Inventors: Alan O. Pittet, Atlantic Highlands; Ranya Muralidhara, Fair Haven, both of N.J.

[73] Assignee: International Flavors & Fragrances Inc., New York, N.Y.

[21] Appl. No.: 231,776

[22] Filed: Feb. 5, 1981

[51] Int. Cl.³ .................... C07C 39/06; C07C 39/18
[52] U.S. Cl. .................................................. 568/780
[58] Field of Search ............................. 568/780, 781; 252/522 R

[56] References Cited

U.S. PATENT DOCUMENTS 4,195,041 3/1980 Kawamura ...................... 568/280

FOREIGN PATENT DOCUMENTS 789996 4/1973 Belgium .

OTHER PUBLICATIONS

Fujimaki et al., "Agric. Biol. Chem.", 41 (9), 1721–1725 (1977).
Walradt et al., "J. Agr. Food Chem.", vol. 18, No. 5 (1970), pp. 926–928.
Lukin et al., "J. Organic Chemistry," vol. 23 (1958), p. 1007.
Pyysalo et al., "Lebensmitte-Wihenschaft Tech.", vol. 10 (1977), p. 36.
Critical Review in Food, "Science and Nutrition", vol. 10 (4), 1978, pp. 335–336.
Carson et al., "J. Org. Chem.", vol. 23, 1958.
Walradt et al., "Ag. and Food Chem.", vol. 19, (5), pp. 972–979 (1971).
Lloyd et al., "Tobacco International", 125 (Summary of Coreste Symposium, 1974, Montreux, Switzerland.
Lloyd et al., "Tobacco Science", XX:43–51 (1976).

Primary Examiner—Werren B. Lone
Attorney, Agent, or Firm—Arthur L. Liberman

[57] ABSTRACT

Described in a process for preparing food grade paravinyl phenol using as a starting material parahydroxybenzaldehyde whereby the parahydroxybenzaldehyde is first reacted with malonic acid and is then decarboxylated in one step to form an impure paravinyl phenol. The impure paravinyl phenol is then acetylated to form paraacetoxy phenol which is separated from the impurities and hydrolyzed thereby yielding food grade, substantially pure, paravinyl phenol.

9 Claims, 23 Drawing Figures

NMR SPECTRUM FOR EXAMPLE I A.

IR SPECTRUM FOR EXAMPLE IA.

GLC PROFILE FOR EXAMPLE IB.

GLC PROFILE FOR EXAMPLE II.

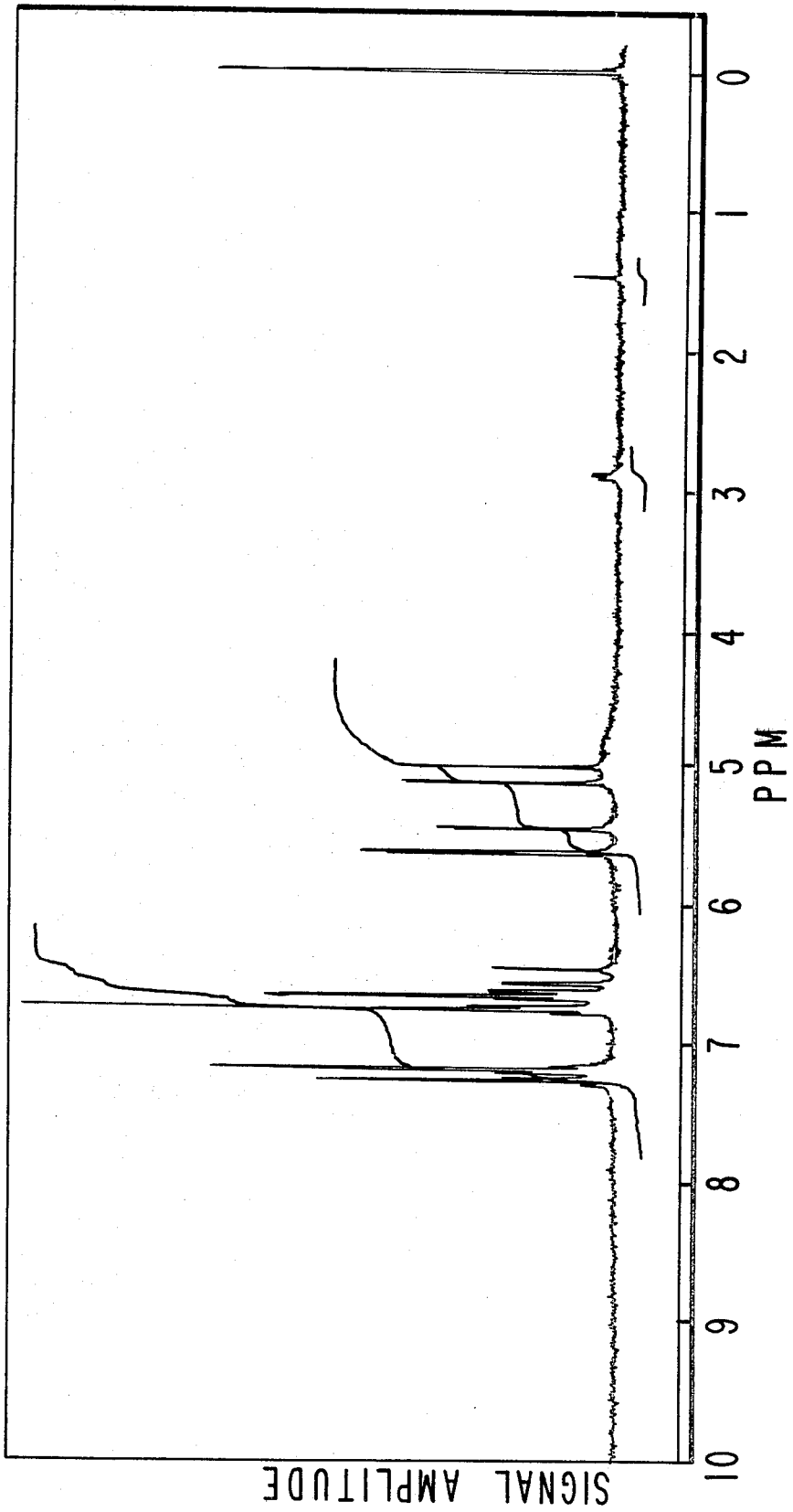

GLC PROFILE FOR EXAMPLE IIIA.

GLC PROFILE FOR EXAMPLE IIIA.

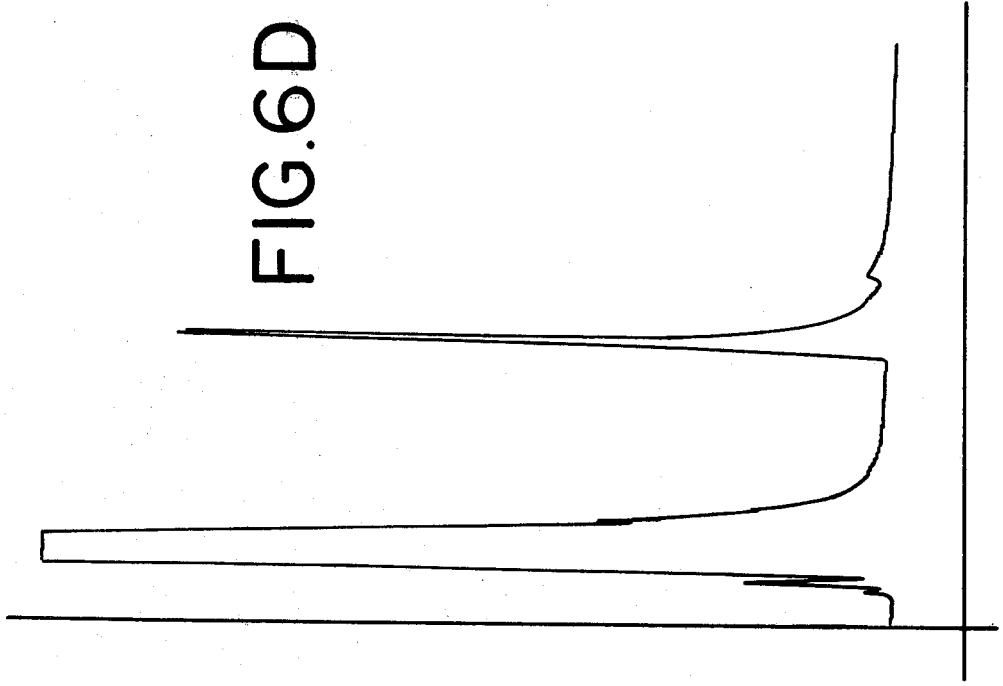
FIG.6D
GLC PROFILE FOR EXAMPLE III A.
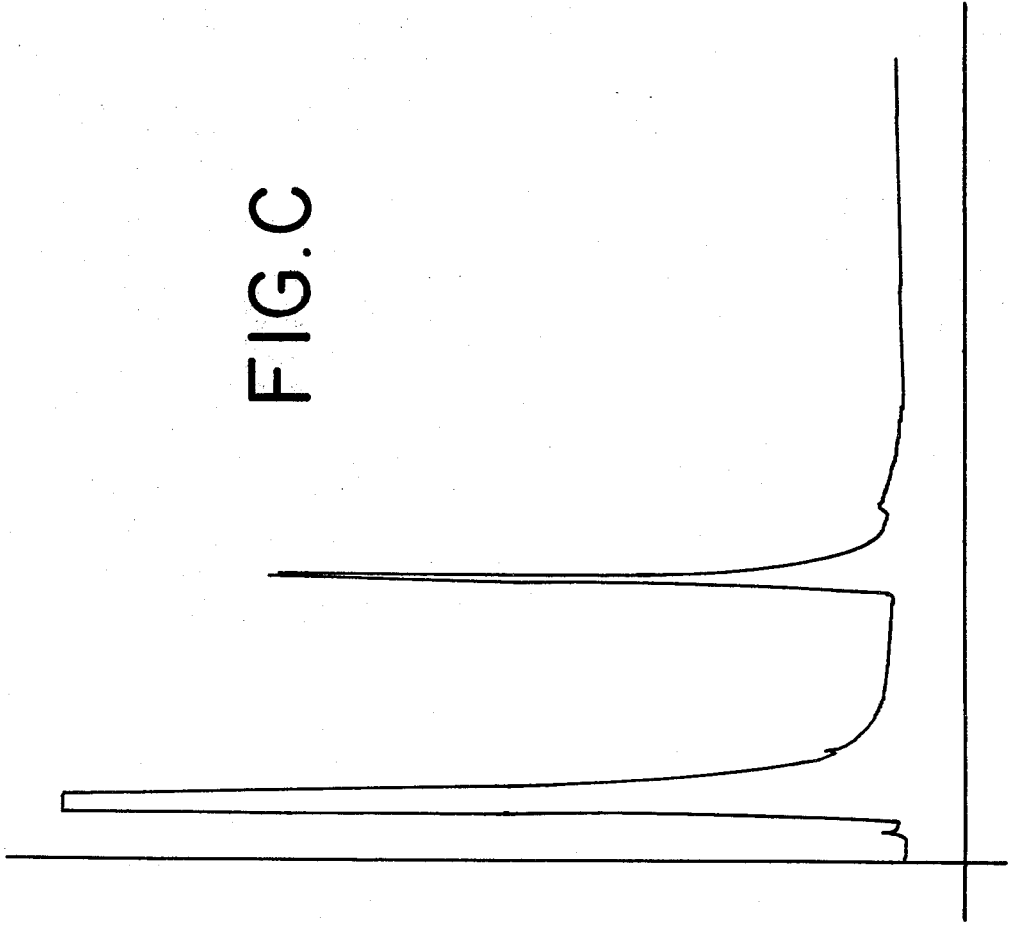
FIG.C
GLC PROFILE FOR EXAMPLE III A.

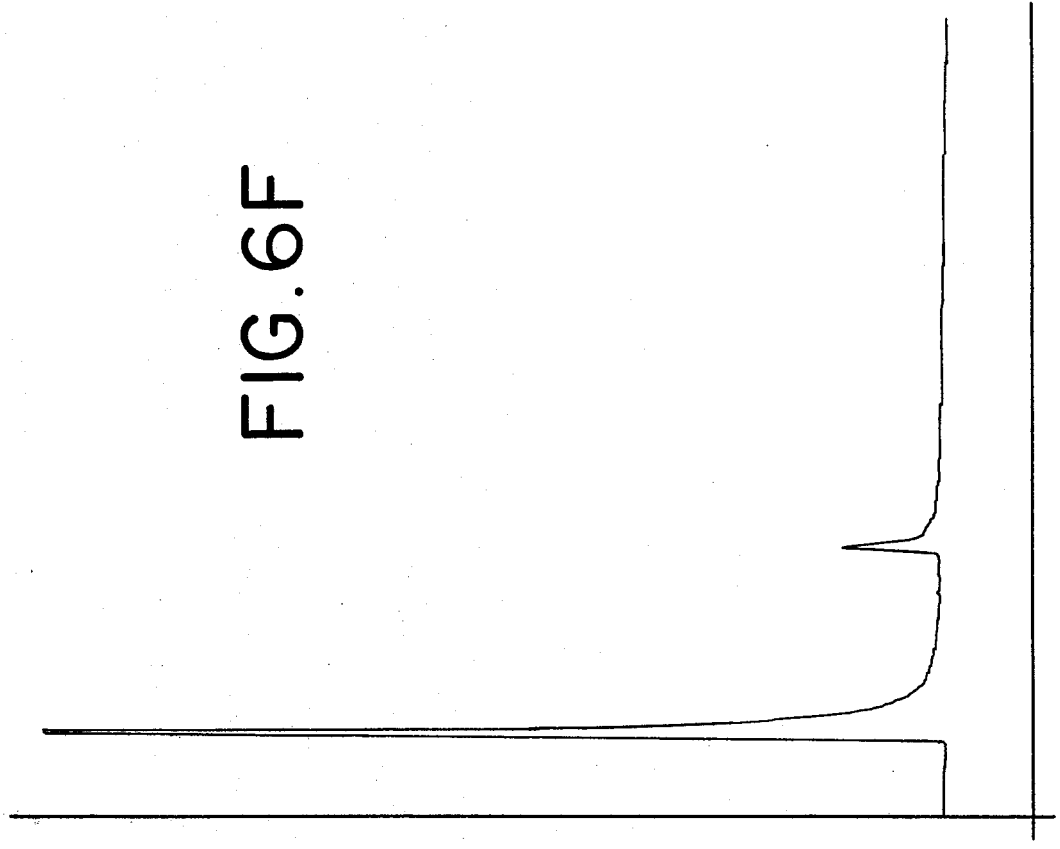
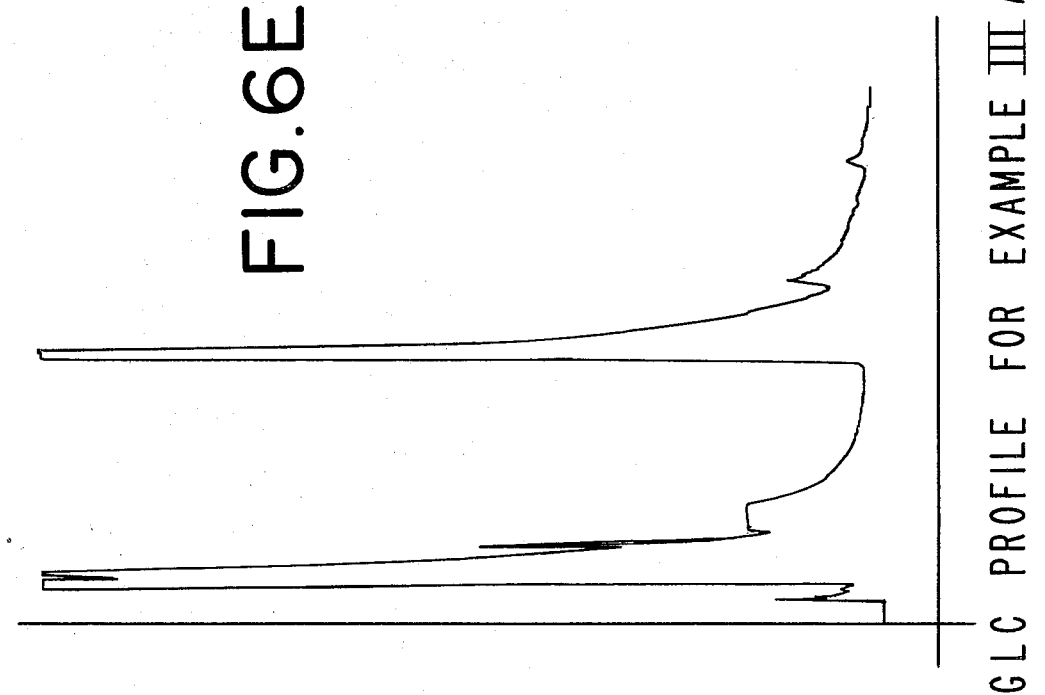

GLC PROFILE FOR FRACTION 5 OF EXAMPLE III A.

GLC PROFILE FOR FRACTION 4 OF EXAMPLE III A.

NMR SPECTRUM FOR FRACTION 2 OF EXAMPLE III B.

IR SPECTRUM FOR EXAMPLE IV C.

GLC PROFILE FOR EXAMPLE VC.

GLC PROFILE FOR EXAMPLE VI E.

IR SPECTRUM FOR EXAMPLE VI C.

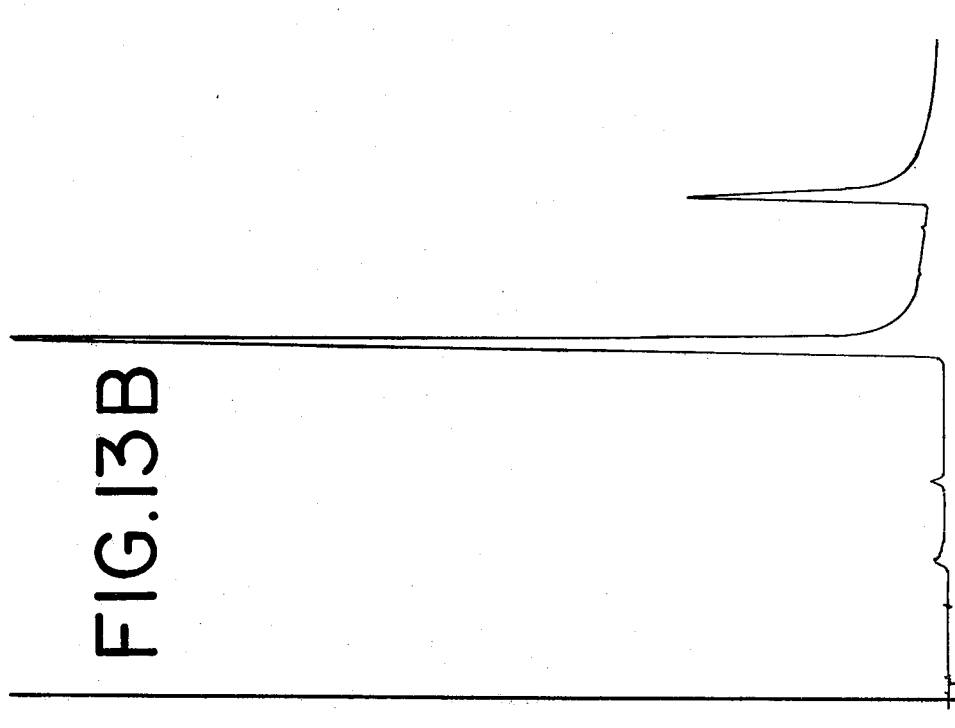
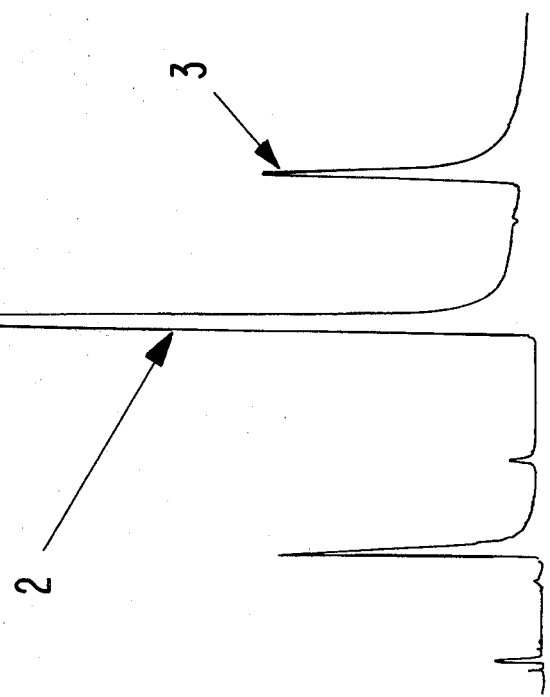

GLC PROFILE FOR FRACTION 3 OF EXAMPLE VII A.

GLC PROFILE FOR EXAMPLE VII.
RESIDUE

PROCESS FOR PREPARING VINYL PHENOL

BACKGROUND OF THE INVENTION

The present invention relates to a novel process for the production of paravinyl phenol by reaction of parahydroxybenzaldehyde with malonic acid followed by decarboxylation all in one step to produce impure paravinyl phenol which is then immediately reacted with an acetylating agent to produce paraacetoxy phenol which is separated from the impurities and hydrolyzed to form food grade paravinyl phenol.

Paravinyl phenol is a highly desirable food flavoring substance. It is known to be present in natural vanilla extract and it is considered by many flavorists in the art to be the key chemical for the flavor in vanilla extract. It is also considered to be important for cocoa, cocoa butter and especially for delicate smoky notes in whiskey and roasted peanuts. In view of the presently high cost of vanilla bean, and inconsistent availability of vanilla extract, the production of food grade paravinyl phenol has become very important. Paravinyl phenol, having the structure:

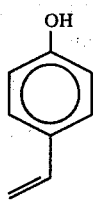

has a vanilla extract-like, cocoa butter-like, cocoa-like, roasted peanut-like and sweet aroma and taste characteristic of 0.5 ppm. Fujimaki et al, Agric. Biol. Chem., 41(9) 1721–1725, 1977, indicates that the paravinyl phenol is present as a volatile phenol in the steam distillate of rice bran. The organoleptic characteristics of paravinyl phenol are set forth in the December 1978 issue of Critical Review in Food, Science and Nutrition 10 (4) 1978 at pages 335–336. Walradt et al identified paravinyl phenol as a constituent of popcorn flavor in J. Agr. Food Chem. Volume 18, No. 5, 1970 at page 926. Paravinyl phenol has also been identified as an aroma constituent of the Cloudberry (*Rubus chamaemorus L.*) in a paper by Pyysalo et al, Lebensmittel-Wiffenschaft Technologie, Volume 10, (1977) at page 36.

Paravinyl phenol is also known to be useful in augmenting the aroma or taste of perfume compositions, perfumed articles and colognes as well as smoking tobaccos and smoking tobacco articles. Thus, insofar as smoking tobacco and smoking tobacco articles are concerned, the paravinyl phenol augments or enhances the earthy, sweet, leathery and vanilla-like aromas of smoking tobaccos in general prior to smoking and on smoking it imparts a smooth, sweet, vanilla-like character to smoke flavor and enhances the body. It is one of the more compatible materials with natural tobaccos known today.

Insofar as augmenting or enhancing the aroma of perfume compositions and perfumed articles, the paravinyl phenol augments or enhances floral, animal-like, waxy aromas and aroma nuances reminiscent of ylang, jasmin, tuberose and karo-karounde. It imparts a very natural-like aroma to other synthetics and it augments or enhances other natural aroma materials.

Previous preparations of paravinyl phenol are well known in the art. Among the more efficient preparations of paravinyl phenol is that disclosed in Belgian Pat. No. 789,996 published on Apr. 12, 1973 (title: "Process for the Decarboxylation of Hydroxyarylcarboxylic Acids") at Example V where it is indicated that parahydroxybenzaldehyde may be reacted with malonic acid in the presence of dimethylformamide, ethylenediamine and benzene to form paravinyl phenol in one step. Although the process is efficient, the product obtained is contaminated with dimethylformamide and the flavor and tobacco uses of this material are nil as a result of the impossibility of separating the dimethylformamide from the paravinyl phenol. Attempts to remove the dimethylformamide by extraction proved to be impossible. Thus, the process disclosed by Belgian Pat. No. 789,996, to wit:

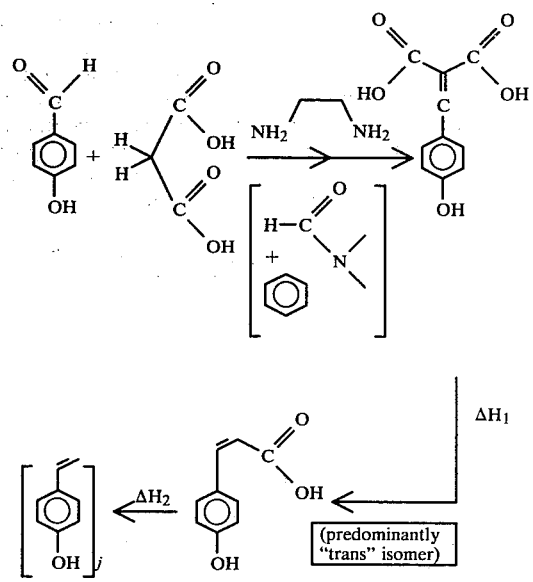

has been found to be incapable of use for the purposes of production of food grade paravinyl phenol, by itself.

Corson et al in a paper entitled "Preparation of Vinylphenols and Isopropenylphenols", volume 23, April, 1958 J. Org. Chem., discribes the process for production of paravinyl phenol going through paraacetoxystyrene according to the reaction sequence:

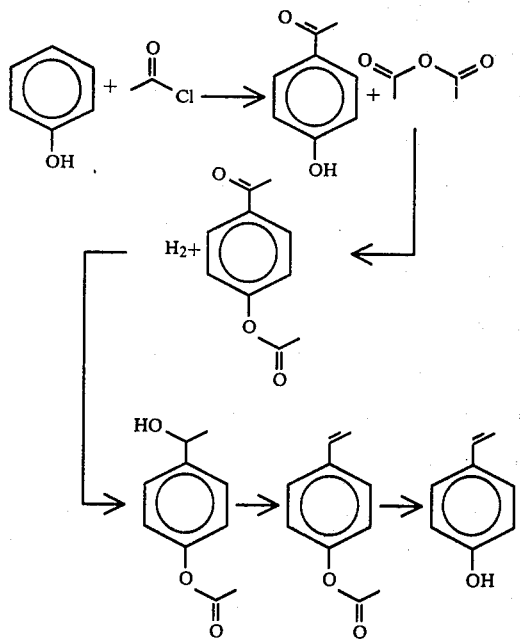

However, this reaction involves a complicated four step process including acylation of phenol to form paraacetyl phenol followed by acylation of the paraacetyl phenol to form paraacetoxyacetophenone followed by hydrogenation of the paraacetoxyacetophenone to form paraacetoxyhydroxyethylbenzene followed by dehydration thereof to form the paraacetoxystyrene followed by hydrolysis to form paravinyl phenol.

Nothing in the prior art, however, indicates the efficient one-step, high yield reaction using the dimethylformamide-ethylenediamine-cyclohexane reaction system followed by acylation of impure paravinyl phenol to form the paraacetoxystyrene followed by subsequent separation and hydrolysis to form food grade paravinyl phenol.

The foregoing reaction sequences and in subsequent reactions the material indicated thusly:

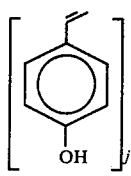

is indicative of impure paravinyl phenol and the material indicated thusly:

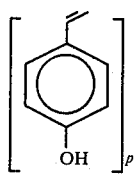

is indicative of food grade paravinyl phenol.

For the purposes of the disclosure herein, the parahydroxybenzaldehyde may be prepared by any process which gives rise to a substance which ultimately gives rise to the food grade paravinyl phenol. Thus, for example, the processes set forth in U.S. Pat. No. 4,195,041 issued on Mar. 25, 1980, may be used in the production of parahydroxybenzaldehyde for the purposes of this disclosure. Thus, the disclosure of U.S. Pat. No. 4,195,041 issued on Mar. 25, 1980, is herewith incorporated herein by reference.

Other publications which are indicative of the potential organoleptic uses of paravinyl phenol are as follows:

i. Walradt et al, Ag. and Food Chem., Vol. 19, 5, pages 972–9 (October 1971), indicating that paravinyl phenol is known to be present in natural peanut flavor.

ii. Walradt et al, J. Agr. Food & Chem., Vol. 18, No. 5, 1970 at page 926, indicating that paravinyl phenol is a constitutent to popcorn flavor.

iii. Lloyd et al, Tobacco International, 125 (Summary of CORESTA Symposium, 1974, Montreux, Switzerland) and Tobacco Science, XX: 43–51, 1976, indicating that paravinyl phenol exists in Flue-cured tobacco flavor.

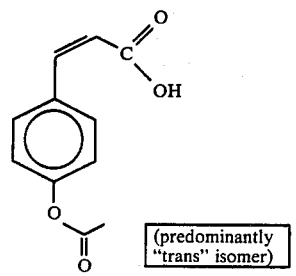

paraacetoxy cinnamic acid produced according to Example IA.

Figure 2:
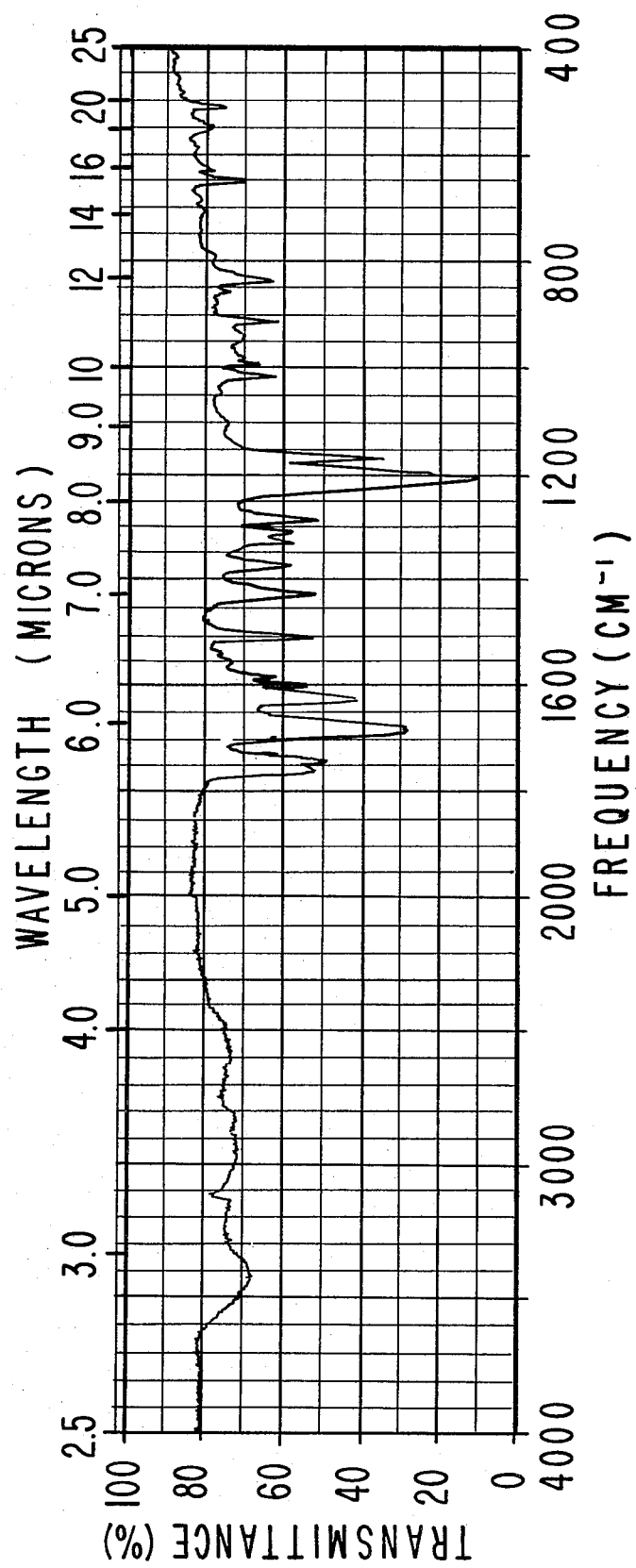

FIG. 2 is the infra-red spectrum for the paraacetoxy cinnamic acid having the structure:

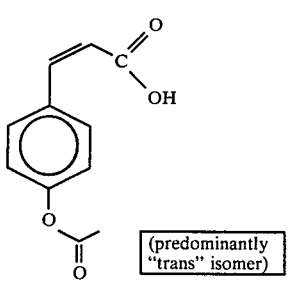

produced according to Example IA.

Figure 3:
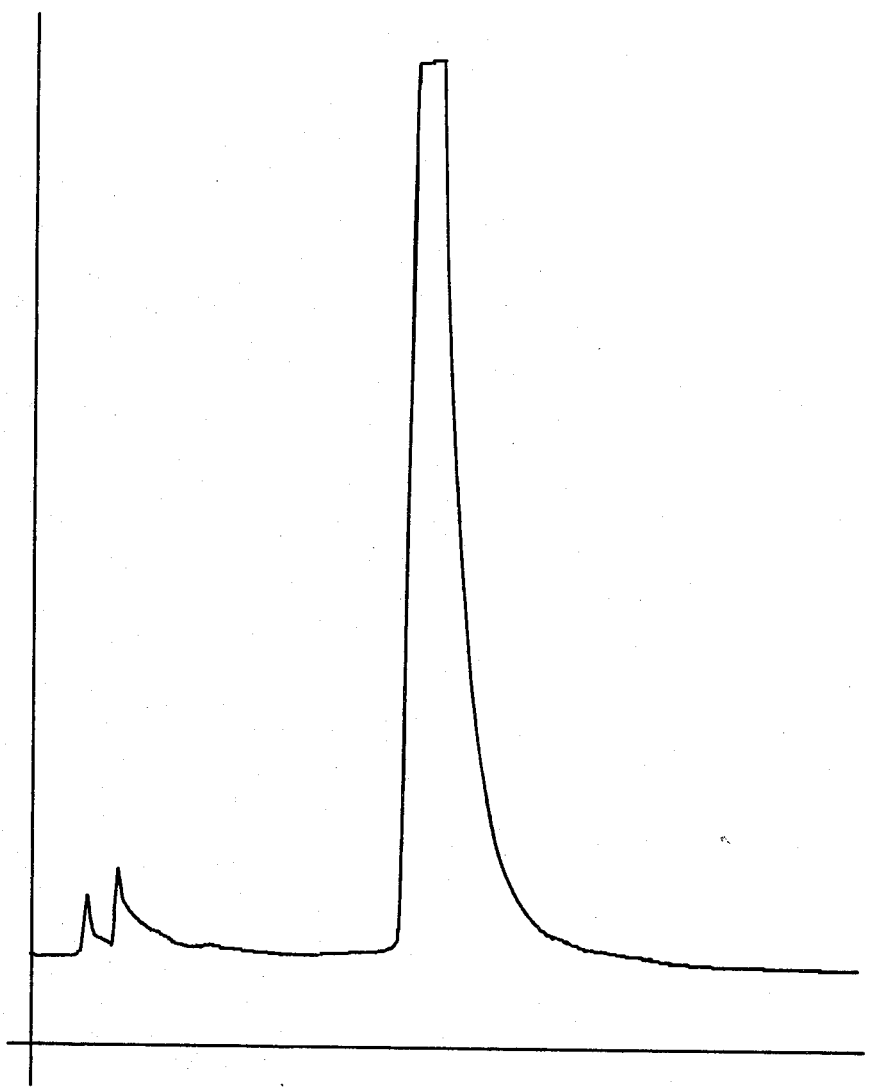

FIG. 3 is the GLC profile for the reaction product produced according to Example IB consisting of paraacetoxy styrene having the structure:

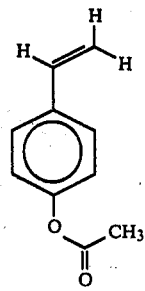

Figure 4:
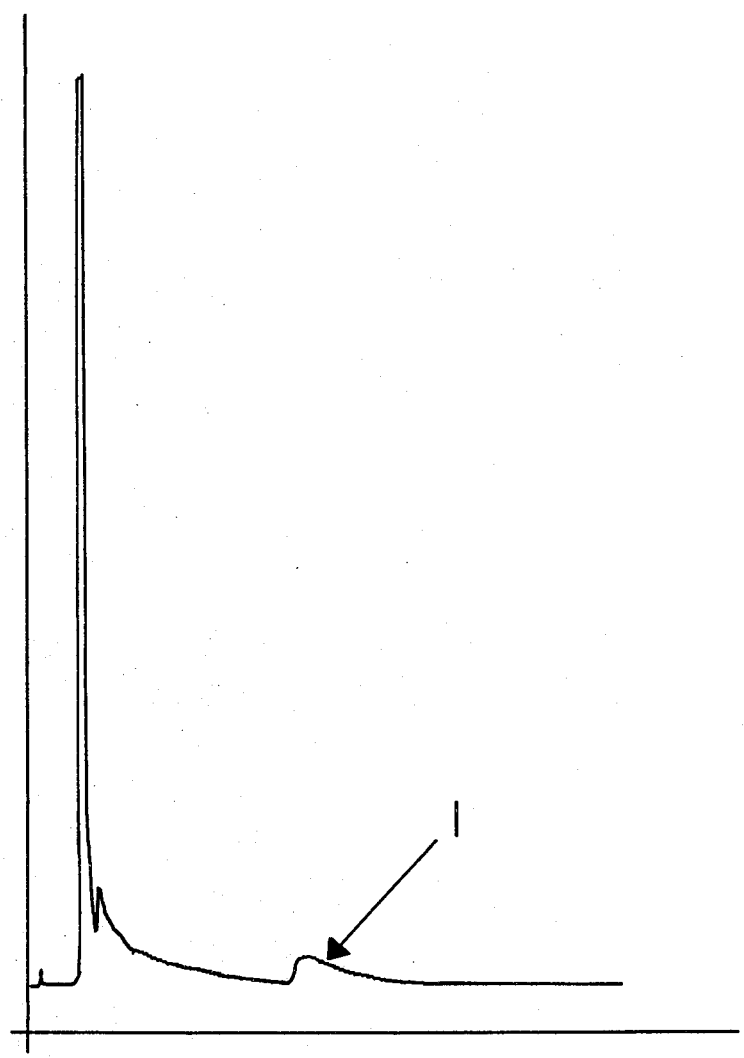

FIG. 4 is the GLC profile for the paravinyl phenol produced according to Example II having the structure:

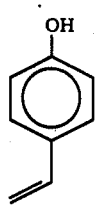

FIG. 5 is the NMR spectrum for the paravinyl phenol produced according to Example II having the structure:

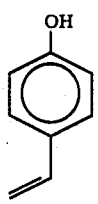

Figure 6B:
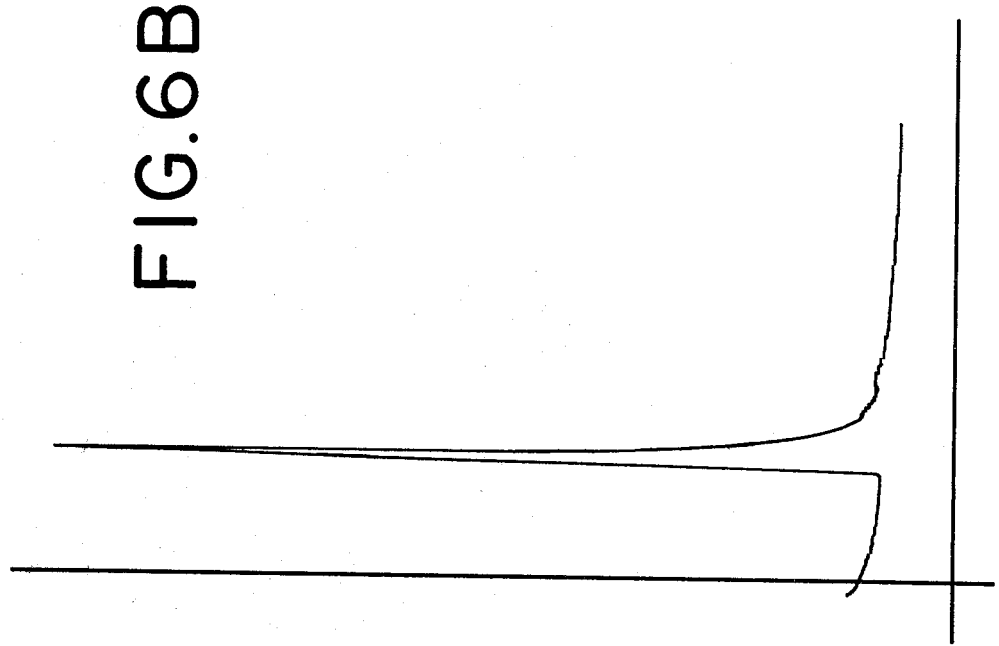
Figure 6A:
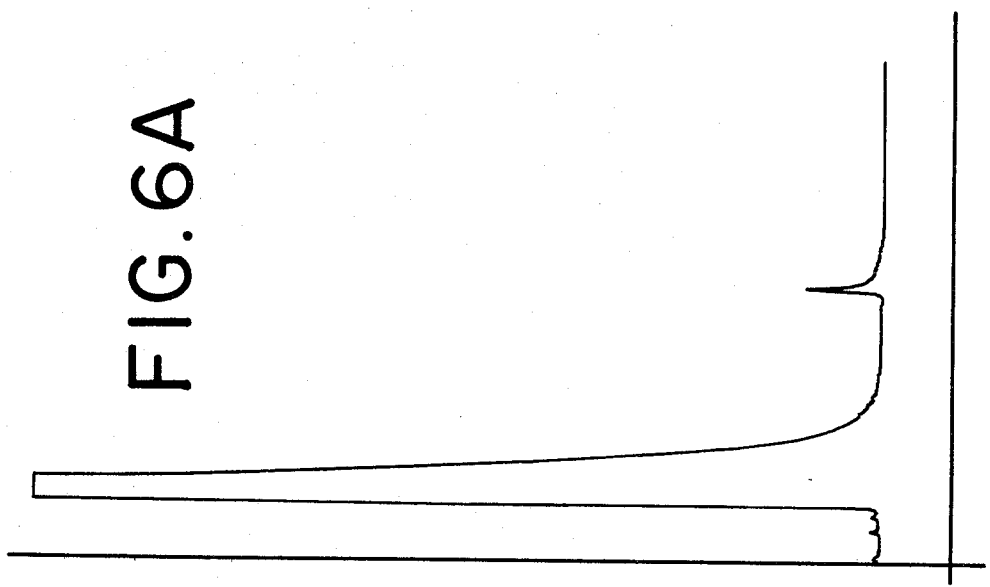

FIG. 6A is the GLC profile for the paravinyl phenol having the structure:

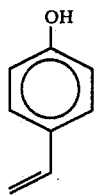

produced according to Example IIIA, contained in the cyclohexane layer in the reaction product.

FIG. 6B is the GLC profile for the paravinyl phenol contained in the heavy oil layer of the reaction product of Example IIIA.

FIG. 6C is the GLC profile for the paravinyl phenol contained in the extract of the heavy oil which extract is the ethyl acetate extract produced according to Example IIIA.

FIG. 6D is the GLC profile for the paravinyl phenol contained in the combined ethyl acetate and cyclohexane extracts of the reaction product of Example IIIA.

FIG. 6E is the GLC profile for the crude reaction product of Example IIIA containing the paravinyl phenol.

FIG. 6F is the GLC profile for fraction 3 of the distillation product of the reaction product of Example IIIA.

Figure 6H:
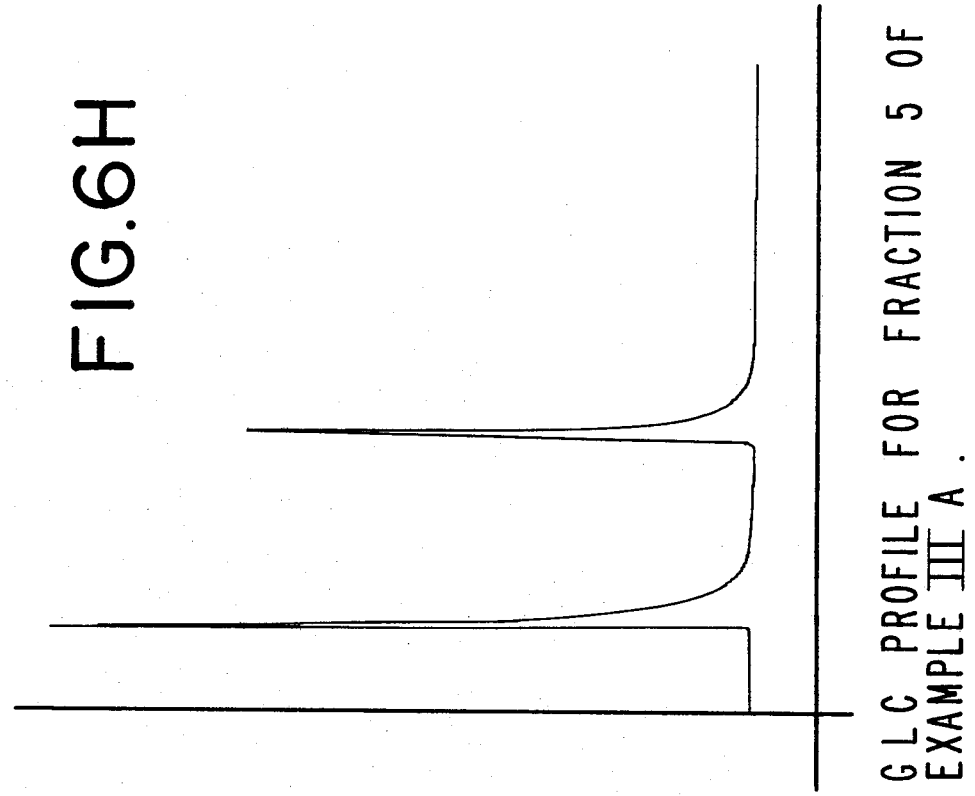
Figure 6G:
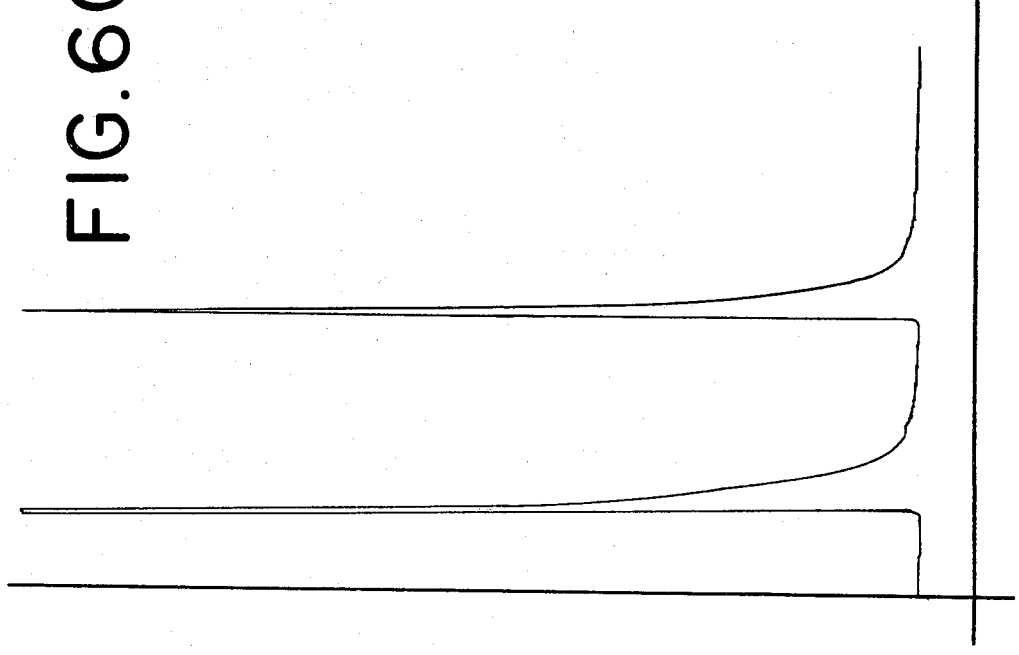

FIG. 6G is the GLC profile for fraction 4 containing paravinyl phenol of the distillation product of the reaction product of Example IIIA.

FIG. 6H is the GLC profile for fraction 5 of the distillation product of the reaction product of Example IIIA containing the paravinyl phenol.

Figure 7:
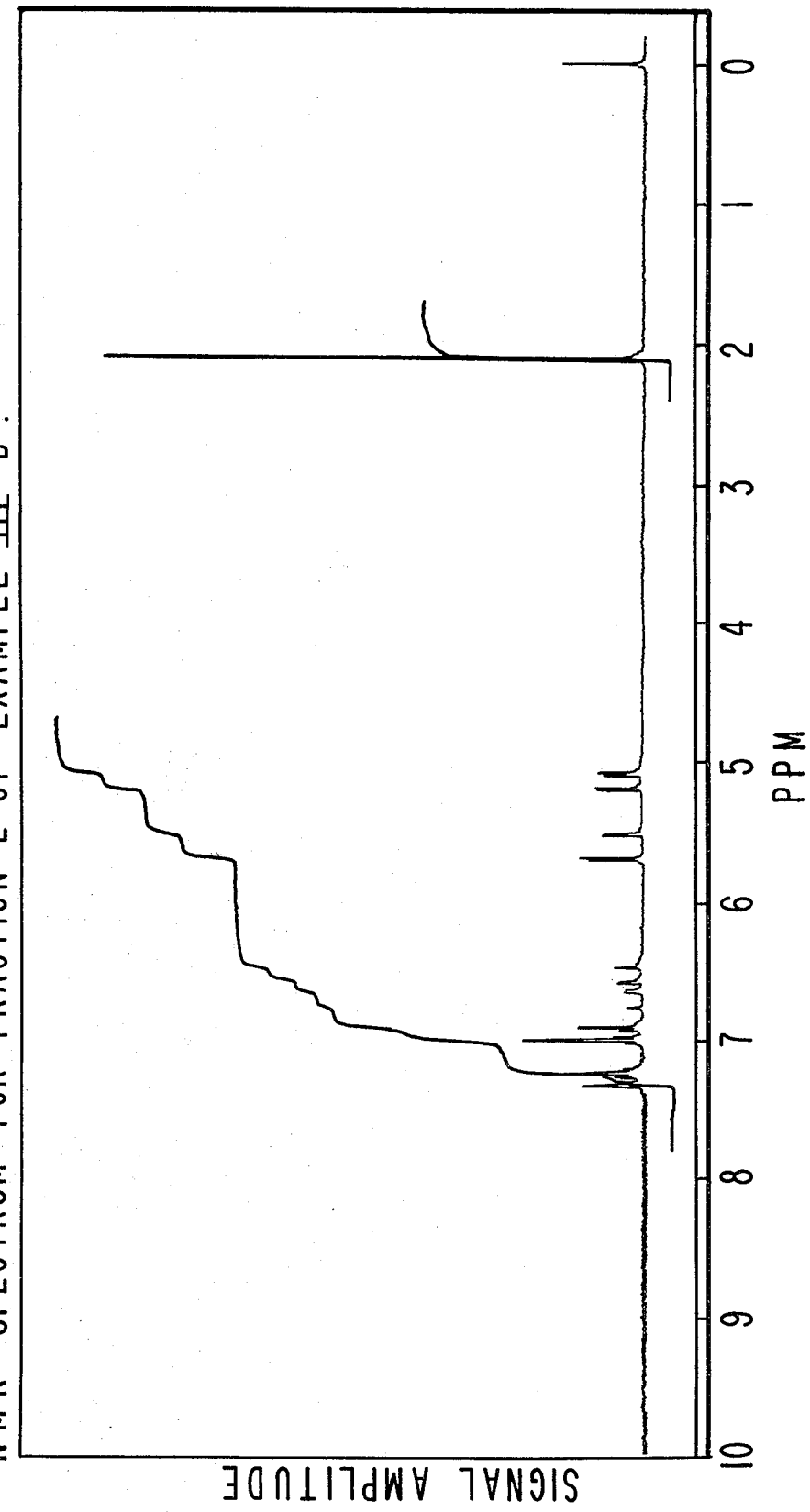

FIG. 7 is the NMR spectrum for fraction 2 of the distillation product of the reaction product of Example IIIB containing paraacetoxy styrene having the structure:

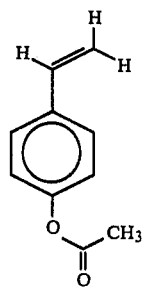

Figure 8:
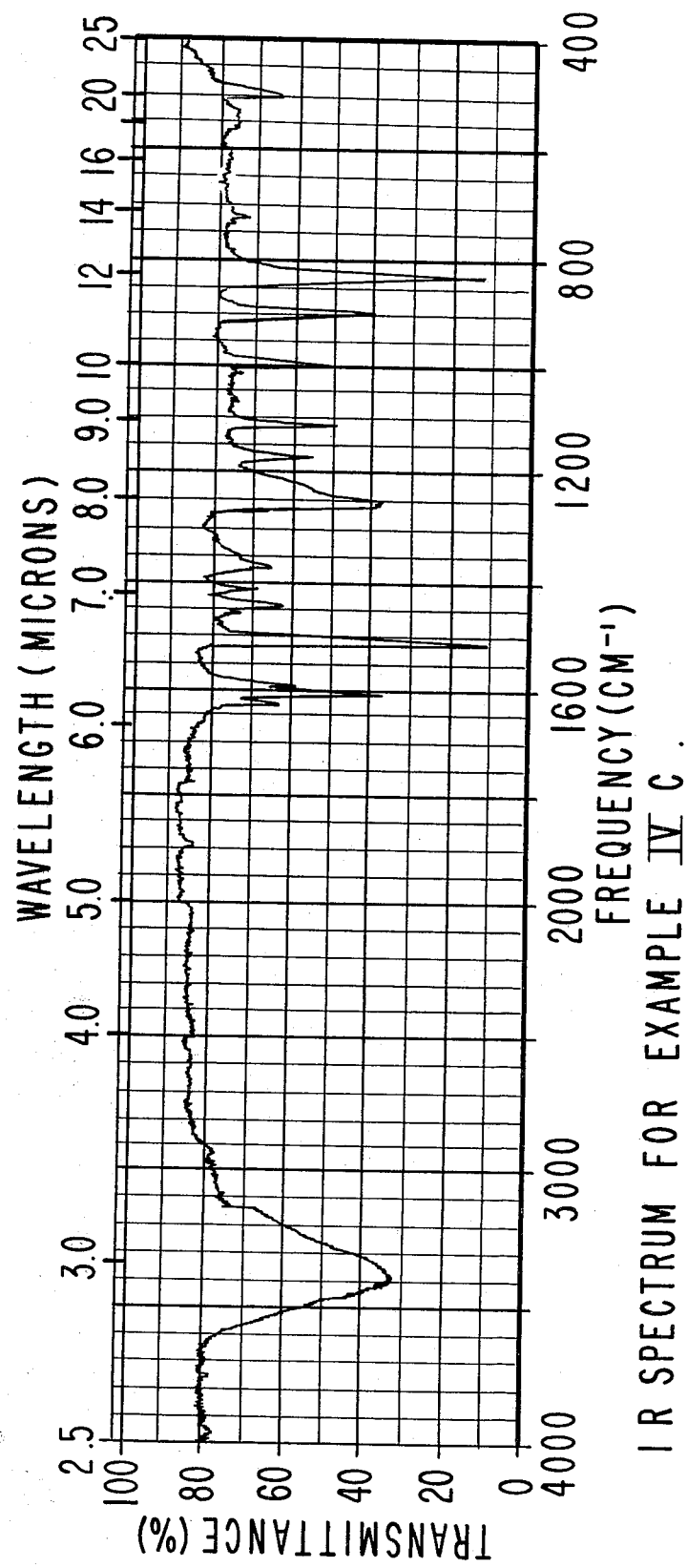

FIG. 8 is the infra-red spectrum for the paravinyl phenol having the structure:

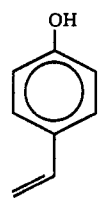

produced according to Example IVC.

Figure 9:
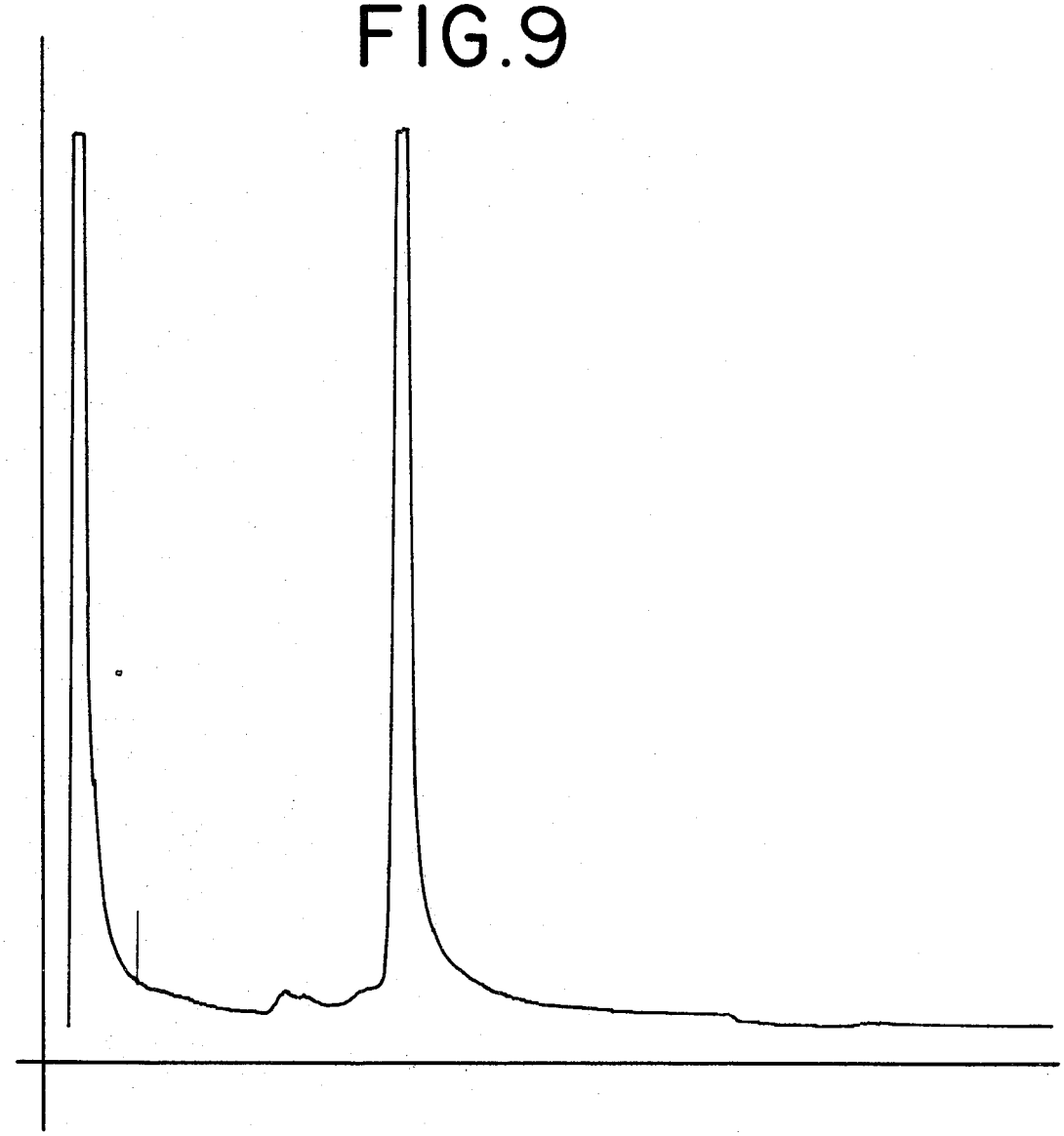

FIG. 9 is the GLC profile for the paravinyl phenol having the structure:

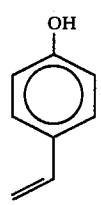

produced according to Example VC.

Figure 10:
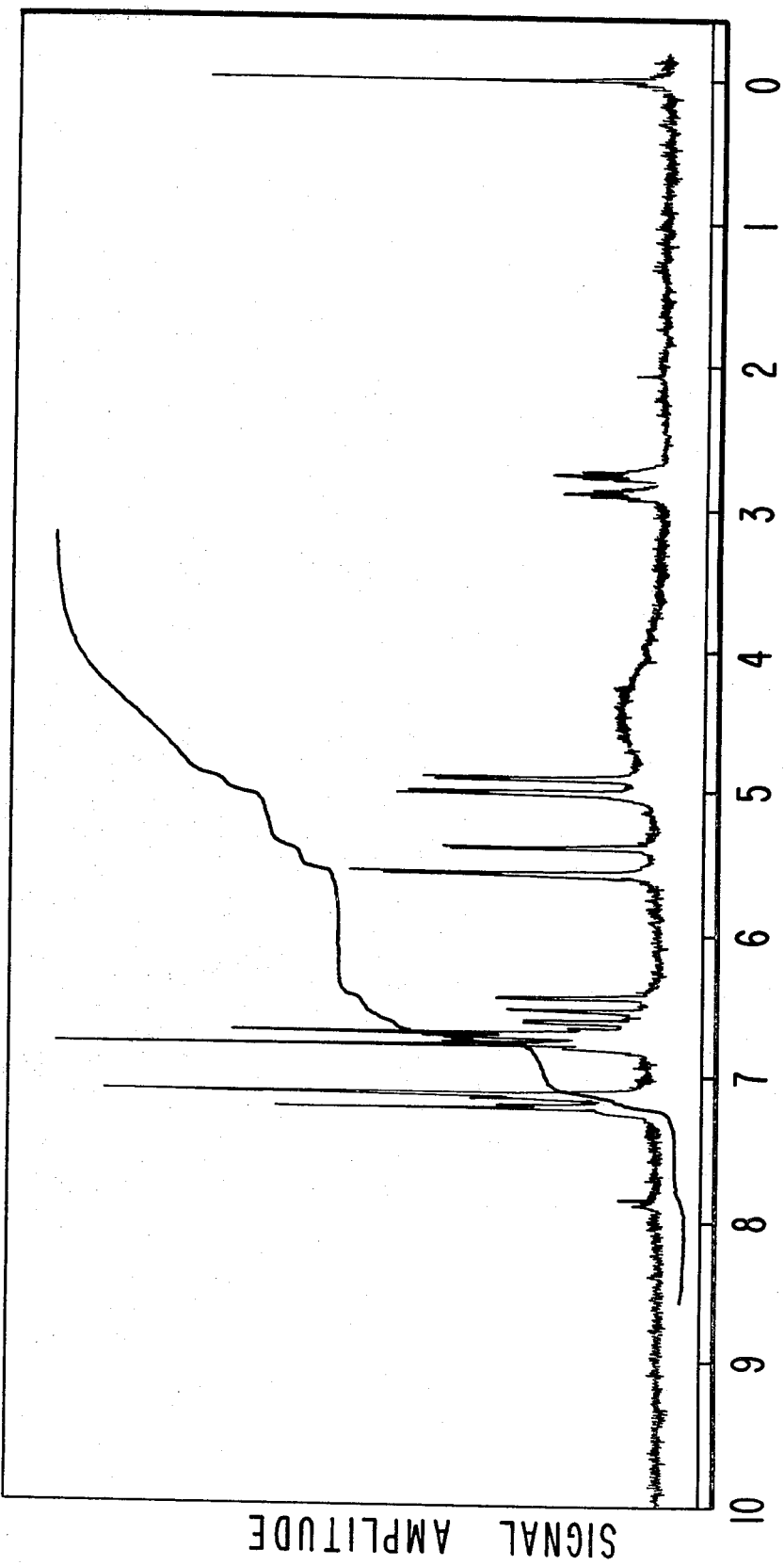

FIG. 10 is the NMR spectrum for the paravinyl phenol produced according to Example VC having the structure:

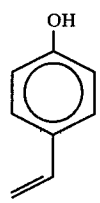

Figure 11:
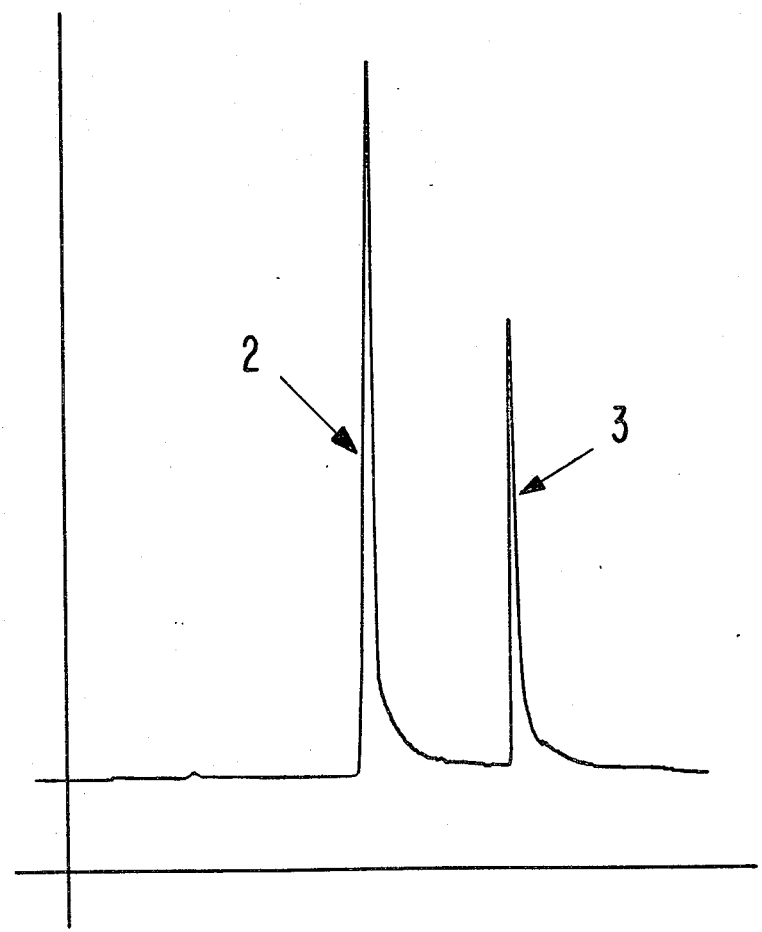

FIG. 11 is the GLC profile for the paraacetoxy styrene having the structure:

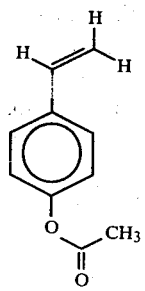

produced according to Example VIB.

Figure 12:
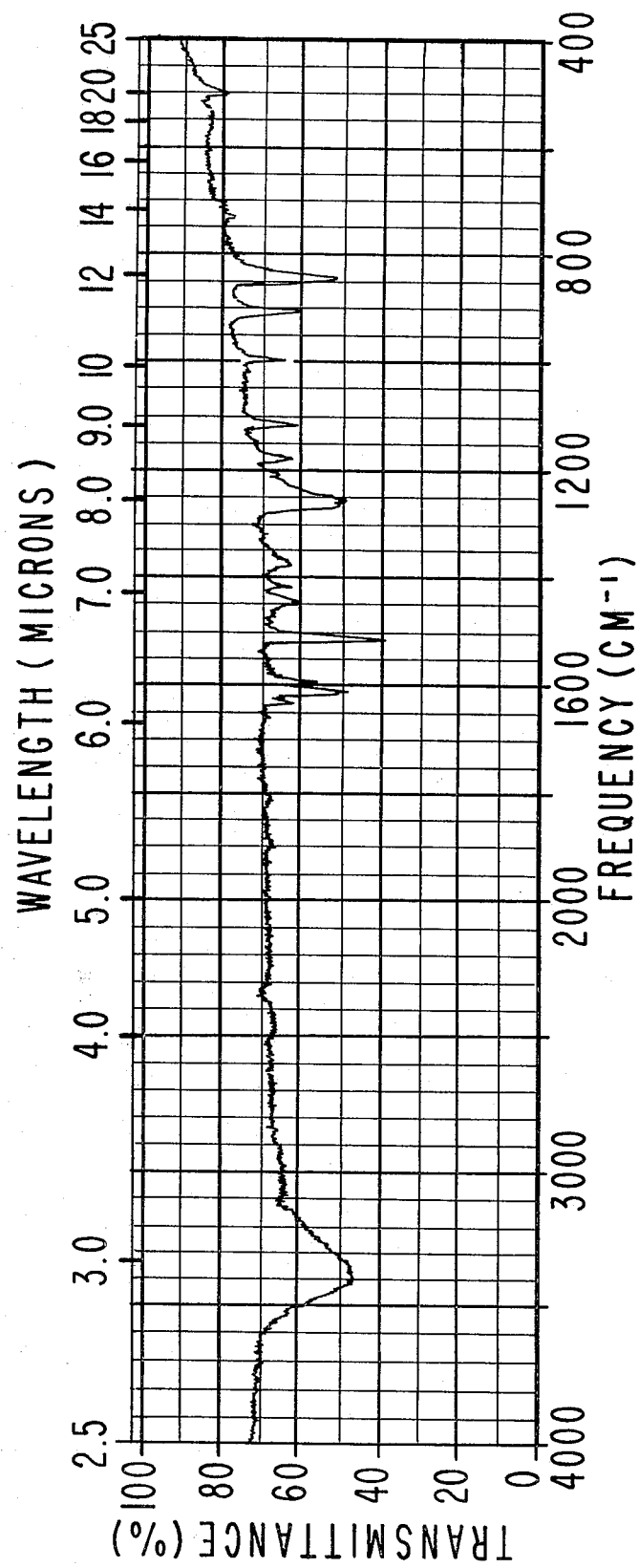

FIG. 12 is the infra-red spectrum for the paravinyl phenol having the structure:

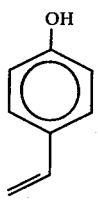

produced according to Example VIC.

FIG. 13A is the GLC profile for fraction 1 of the distillation product of the reaction product of Example VII containing the compounds paravinyl phenol and paraacetoxy styrene having the structures, respectively:

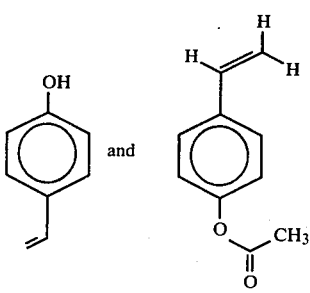

FIG. 13B is the GLC profile for fraction 2 of the distillation product of the reaction product of Example VII containing the compounds having the structures:

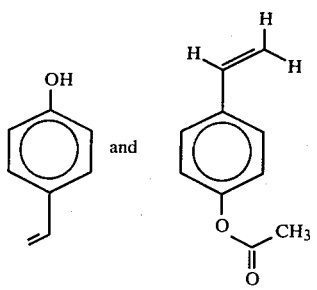

Figure 13C:
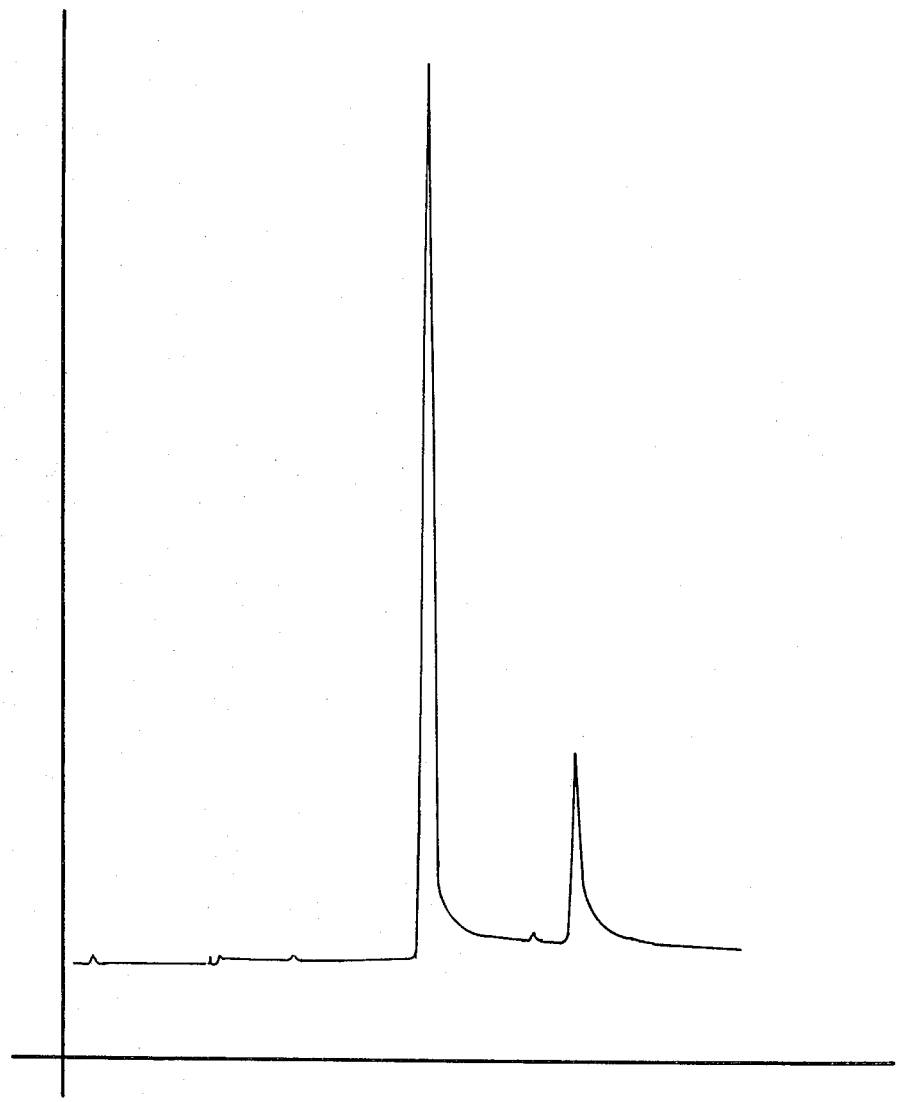
Figure 13D:
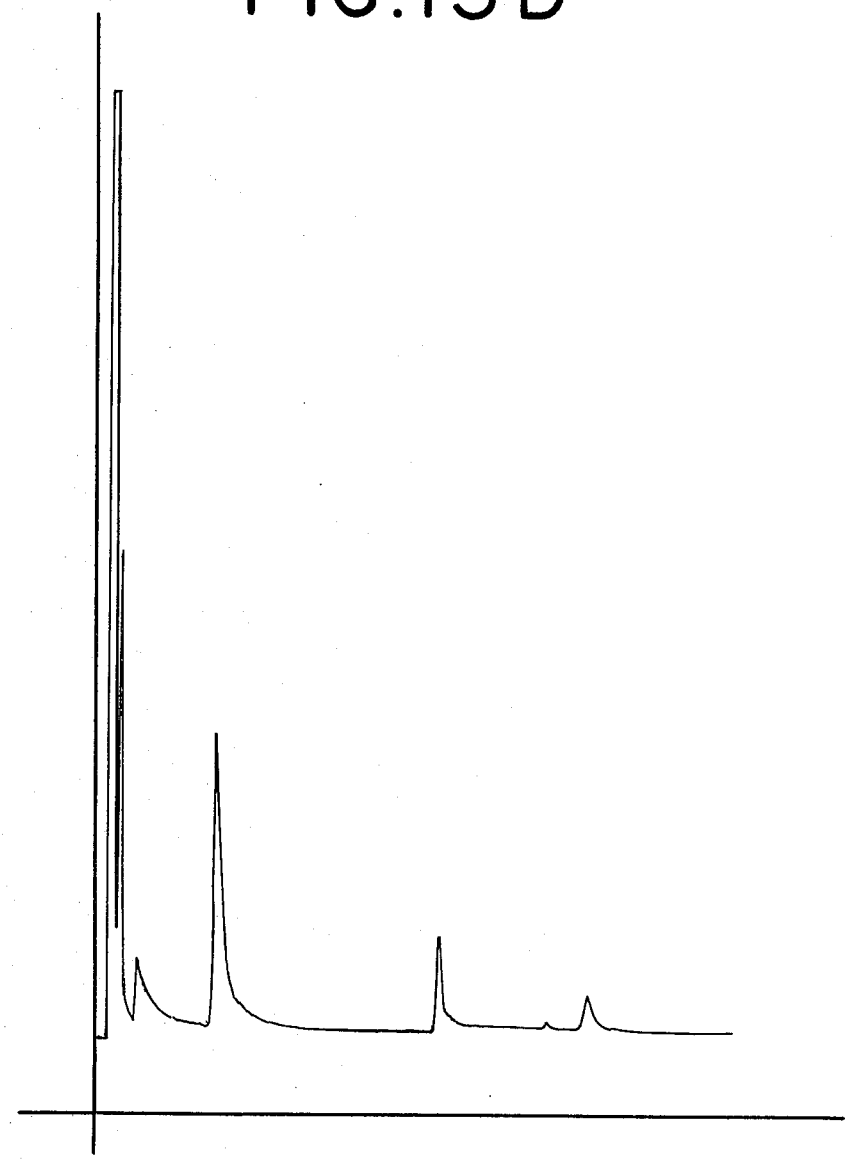

FIG. 13C is the GLC profile for fraction 3 of the distillation product of the reaction product of Example VII containing the compounds having the structures:

FIG. 13D is the residue of the distillation product of the reaction product of Example VII containing the compounds having the structures:

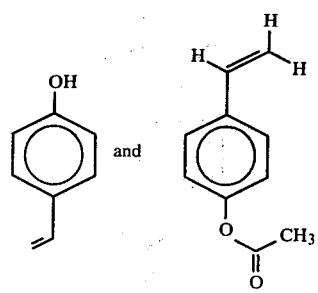

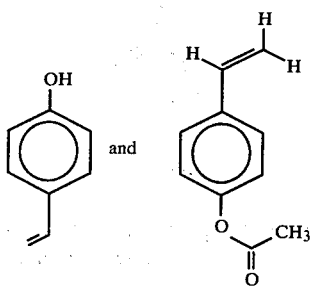

DETAILED DESCRIPTION OF THE DRAWINGS, FIGS. 4 AND 13A

In FIG. 4 which represents the GLC profile for the reaction product of Example II containing paravinyl phenol having the structure:

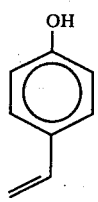

the peak referenced with the numeral "1" indicates the said paravinyl phenol.

In FIG. 13A which is the GLC profile for fraction 1 of the distillation product of Example VII (conditions: Carbowax 10'×⅛" column programmed at 100°–220° C. at 8° C. per minute), the peak indicated using the reference numeral "2" is the compound paraacetoxy styrene having the structure:

and the peak indicated by the reference numeral "3" represents the compound, paravinyl phenol, having the structure:

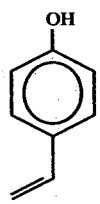

THE INVENTION

The present invention provides a process for the manufacture of food grade paravinyl phenol using as a starting material parahydroxybenzaldehyde. Paravinyl phenol has the structure:

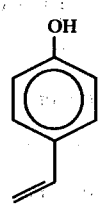

Parahydroxybenzaldehyde has the structure:

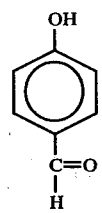

Briefly, our invention involves first the formation in situ or in separate reactions of an impure form of parahydroxy phenol designated thusly:

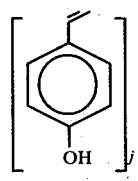

and then subsequent purification of the impure paravinyl phenol by means of acetylation of the hydroxyl moiety to form a food grade paravinyl phenol indicated thusly:

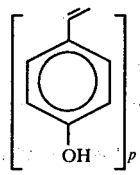

The process of our invention involves first the reaction of malonic acid having the structure:

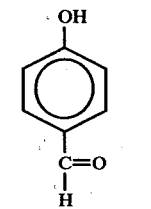

with parahydroxybenzaldehyde having the structure:

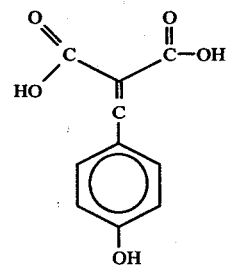

in the presence of ethylenediamine, dimethyl formamide and a cyclohexane solvent to form parahydroxy styrene dicarboxylic acid having the structure:

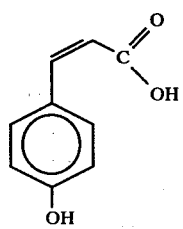

This material is then decarboxylated in situ according to our process to form the parahydroxy cinnamic acid having the structure:

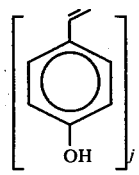

(predominantly "trans" isomer)

In situ, or separately, this parahydroxy cinnamic acid is then decarboxylated to form the impure parahydroxy phenol designated by the structure:

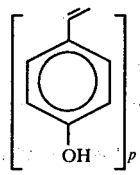

This impure parahydroxy phenol is then reacted with acetic anhydride to form the paraacetoxy styrene which is then separated from the reaction mass as by distillation. The resulting pure paraacetoxy styrene is then hydrolyzed with base such as sodium hydroxide or potassium hydroxide to form the base salt of parahydroxy phenol designated by the structure:

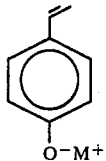

wherein M is sodium or potassium. This salt is then neutralized with acid to form the food grade paravinyl phenol designated by the structure:

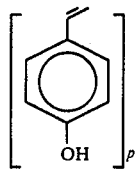

The resultant product is isolated by means of crystallization followed by filtration.

Thus, the reaction sequences of our invention are as follows:

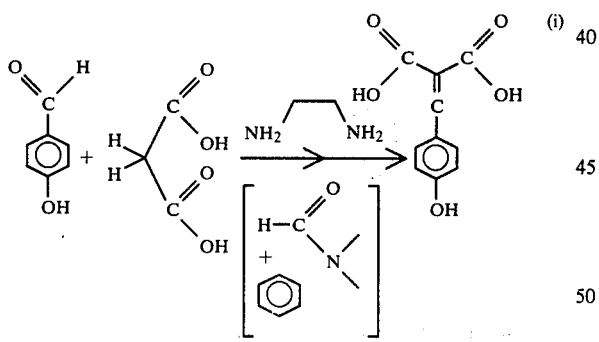

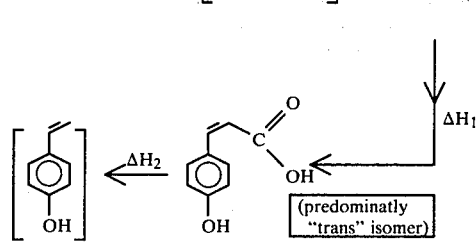

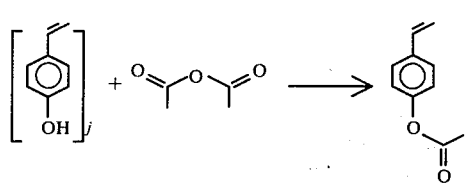

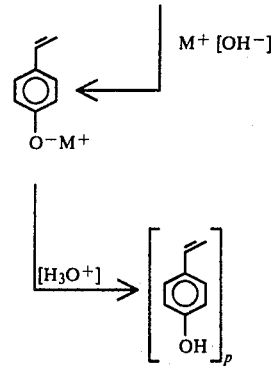

Previous attempts to produce paravinyl phenol in food grade form according to Belgian Pat. No. 789,996 using ethylenediamine, dimethyl formamide and a benzene solvent failed to yield paravinyl phenol in a food grade form. Thus, Belgian Pat. No. 789,996 indicates the reaction:

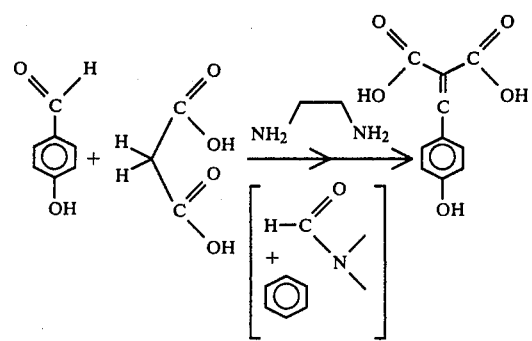

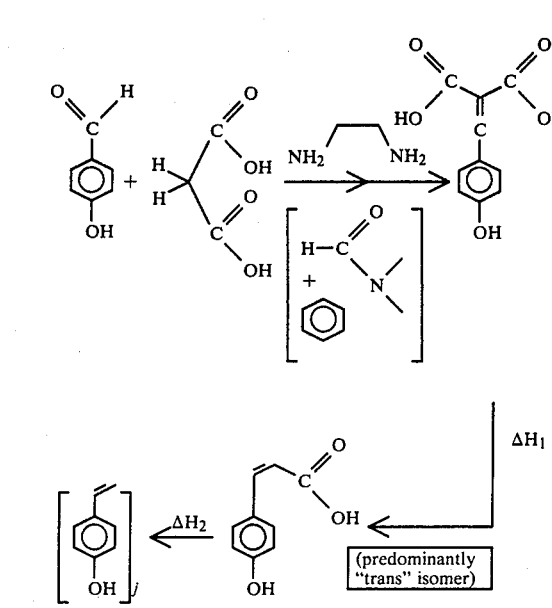

Corson et al "Preparation of Vinylphenols and Isopropenylphenols" Volume 23, April 1958, Journal of Organic Chemistry, required a rather complex process going through the paraacetoxy styrene to make paravinyl phenol, but this did not involve the one step in situ reaction of parahydroxybenzaldehyde with malonic acid but instead involved the reaction sequence:

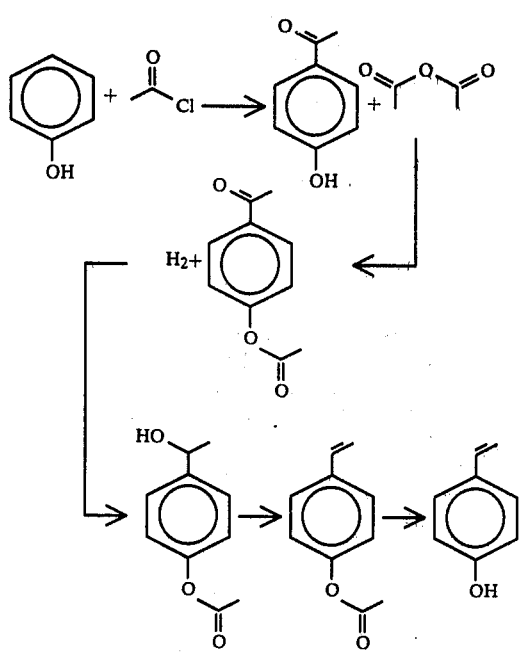

Sovish et al in J. Org. Chem. 24 1345 (1959) shows the preparation of paravinyl phenol by reacting parahydroxy-benzaldehyde with malonic acid in pyridine and xylene to provide parahydroxy cinnamic acid and then decarboxylating the acid with copper-quinoline catalyst to provide the vinyl phenol. The yield is stated to be 41% and the product is indicated to be then crystallized for purification. This reaction does not produce food grade paravinyl phenol. An attempt was made (see Examples IA and IB, infra) to follow the Sovish process using paraacetoxy cinnamic acid having the structure:

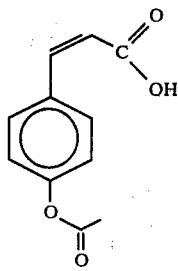

rather than parahydroxy cinnamic acid having the structure:

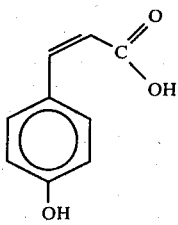

as a starting material according to the reactions:

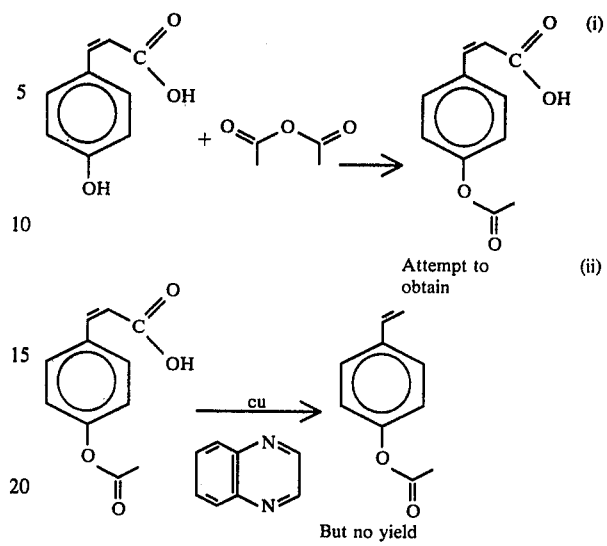

The yield of paraacetoxy styrene using the copper-quinoline catalyst from paraacetoxy cinnamic acid as a starting material was nil, however, as will be seen from Example IB, infra. Attempts using p-hydroxycinnamic acid likewise failed to yield the desired product.

Thus, the range of conditions of reactions set forth supra and infra and in the examples is critical in producing food grade paravinyl phenol.

In carrying out the first phase of our reaction, to wit:

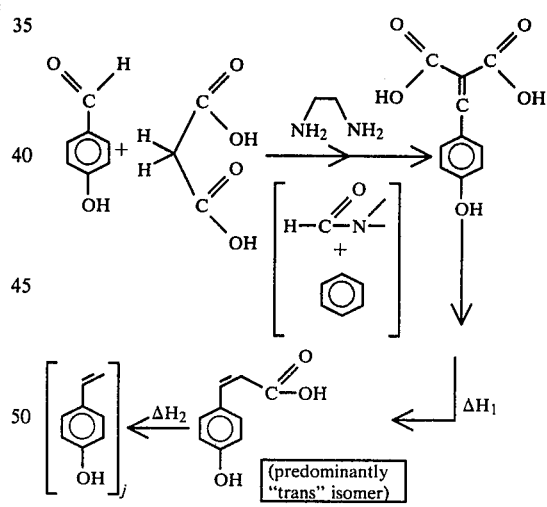

the reaction apparatus is such that water of reaction can be removed during the procedure of the reaction while the malonic acid is reacting with the parahydroxybenzaldehyde. The reaction is to be carried out under reflux conditions and the reflux temperature is a function of the pressure over the reaction mass and the ratio of the five materials in the reaction mass, that is, the parahydroxybenzaldehyde:malonic acid:ethylenediamine:-dimethyl formamide:cyclohexane. As a general rule, during the reaction, the reflux temperature will vary from about 75° C. up to about 80° C. when the reaction is run at atmospheric pressure and will be higher at super atmospheric pressures. No advantage has been ascertained in running the reaction at either sub-atmospheric or super-atmospheric pressures. It is most preferable and most economical to carry out the reaction at atmospheric pressures, that is, at temperatures in the range of from about 75° C. up to about 80° C.

The weight ratio of cyclohexane:parahydroxybenzaldehyde may vary from about 3:1 to about 1.2:1 with a preferred weight ratio of cyclohexane:parahydroxybenzaldehyde being in the range of about 1.8:1 up to about 2.6:1. The weight ratio of parahydroxybenzaldehyde:malonic acid may vary from about 1.5:1 down to about 1:1 with a weight ratio of about 1.2:1 to 1.05:1 being preferred. The weight ratio of parahydroxybenzaldehyde:dimethyl formamide may vary from about 1:4 up to about 1:1 with a preferred ratio of parahydroxybenzaldehyde:dimethyl formamide being from about 1:3 to about 1:1.25.

The weight ratio of ethylenediamine catalyst:parahydroxybenzaldehyde may vary from about 5:1000 up to 5:100 with a preferred ratio of 5:200 up to 5:300 (e.g., a preferred ratio of 2.5 grams of ethylenediamine per mole of parahydroxybenzaldehyde is most preferred).

After all of the water of reaction is removed and refluxing ceases, the reaction mass temperature is raised to a point where the cyclohexane solvent is removed, that is, 85°–90° C. at atmospheric pressure.

It has been previously ascertained that toluene as a solvent cannot be properly used since it forms too much residue because of the higher refluxing temperature at which the reaction is carried out (when carried out at atmospheric pressure). This will be seen by an examination of Example II, infra.

While the cyclohexane solvent is being stripped off, the volume of the solvent in the reaction mass is preferably (but need not be) maintained constant by adding back thereto an equivalent volume of dimethyl formamide having the structure:

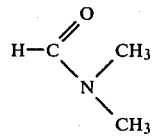

After all of the cyclohexane solvent is removed, the reaction mass is then heated to 115°–118° C. for decarboxylation and at a temperature in the range of from 115° up to 120° C., the decarboxylation is carried out in situ yielding the impure paravinyl phenol product to the reaction mass.

To this impure paravinyl phenol reaction may be added dimethyl formamide to dilute the thick reaction mixture so that it can be added to a significant quantity of water to facilitate the resulting extraction.

At this point a lower alkyl ester such as, and most preferably, ethyl acetate, is used to extract the paravinyl phenol from the body of the aqueous dimethyl formamide solution. After washing the ethyl acetate extract with water and drying same, the ethyl acetate is removed and the crude paravinyl phenol is reacted with acetic anhydride after first mixing same with a base such as sodium hydroxide or potassium hydroxide. The resulting p-acetoxy styrene having the structure:

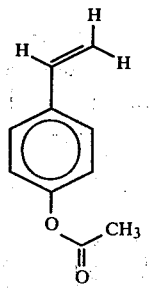

is then extracted from the reaction mass with a volatile solvent such as diethylether and the ether extracts are dried and the solvent stripped to yield a material which is then fractionally distilled to yield the product: paraacetoxy styrene.

The paraacetoxy styrene having the structure:

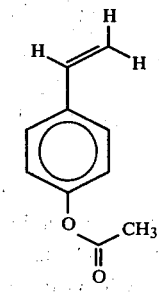

is then reacted with strong base such as potassium hydroxyde or sodium hydroxyde, preferably in aqueous solution. The reaction of the paraacetoxy styrene with base is preferably at a temperature in the range of from about 35° C. up to about 50° C. (below 35° C., the reaction mass forms two layers which gives rise to an incomplete reaction) and the base is preferably in aqueous solution, preferably from about 7% up to about 12% by weight of base, either sodium or potassium hydroxide in water. After the paraacetoxy styrene is hydrolyzed to form the alkali metal salt of parahydroxy phenol having the structure:

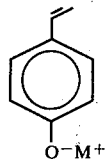

wherein M is sodium or potassium, the pH of the resulting solution is adjusted with acid, preferably weak acid such as acetic acid, whereby the pH is adjusted to 6. At this point, parahydroxy phenol will precipitate out and can be filtered from the reaction mass to yield food grade parahydroxy phenol. The filtered solid is appropriately washed in order to remove any residual acid present resulting from the pH adjustment.

Insofar as the reaction of the impure paravinyl phenol with the acetic anhydride is concerned, the paravinyl phenol is first admixed with dilute base, preferably a 1–4% solution of sodium, potassium or lithium hydroxide. The reaction of acetic anhydride with paravinyl phenol/aqueous base mixture takes place preferably at ambient temperatures and pressures, e.g., 20°-30° C. at atmospheric pressure.

At levels of between 0.1 ppm and 50 ppm, the paravinyl phenol thus produced may be used to augment or enhance the aroma or taste of peanut flavors, apple flavors, passion fruit flavors and whiskey flavors or peanut flavored foodstuffs, apple flavored foodstuffs and beverages, passion fruit flavored foodstuffs and beverages and whiskey flavored beverages and, in addition, vanilla, cocoa, cocoa butter, chocolate, clove, bacon and rum flavored foodstuffs and beverages. Furthermore, the paravinyl phenols thus produced may also be used to augment or enhance the aroma or taste of smoking tobacco and smoking tobacco flavors both prior to and on smoking in the mainstream and the sidestream.

The following Examples I and II are set forth, infra, in order to show techniques attempted to produce paravinyl phenol in food grade form but which were unsuccessful. The following Examples III–VII set forth actual illustrative embodiments of our invention as it is presently preferred to practice it. It will be understood that Examples III–VII are illustrative and the invention is not considered to be restricted thereto except as indicated in the appended claims.

EXAMPLE I
ATTEMPTED PREPARATION OF PARAVINYL PHENOL
(EXAMPLE I(A))

Reaction:

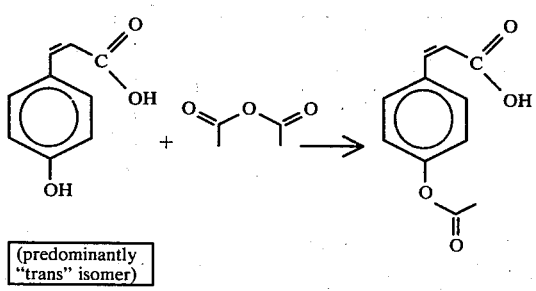

(EXAMPLE I(B))

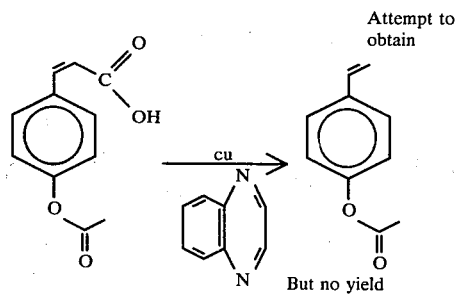

EXAMPLE I(A)

Preparation of Paraacetoxy Cinnamic Acid

Into a 5 liter reaction flask equipped with electric stirrer, cooling bath, thermometer, addition funnel and Buchner funnel, are charged 306 grams (3.0 moles) of acetic anhydride and 164 grams (1.0 moles) of parahydroxy cinnamic acid. The reaction mass is stirred for 15 minutes to allow the acid to dissolve. The acetic acid is added over a period of 15 minutes. NMR and IR spectra confirm that the resulting solid precipitate is paraacetoxy cinnamic acid having the structure:

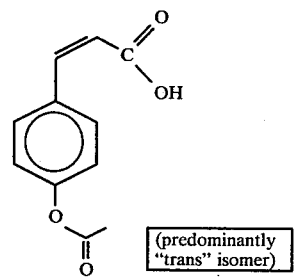

Paraacetoxy cinnamic acid is filtered from the reaction mass.

EXAMPLE I(B)

Into a 500 ml reaction flask equipped with electric stirrer, reflux condenser, thermometer, thermal watch heating mantle, and primal bubbler hooked up to reflux condenser topped to monitor $CO_2$ evolution, is added 50 ml quinoline and 5 grams of copper powder. The quinoline/copper powder mixture is heated to 220° C. While maintaining the reaction mass at 220° C., 25 grams of paraacetoxy cinnamic acid prepared according to Example IA is added to the reaction flask through a powder funnel. The reaction mass is then maintained at 120° C. for a period of 10 minutes and cooled to room temperature. The copper is filtered and a GLC profile (conditions: SE-30 column $8' \times \frac{1}{4}''$ programmed at 100°-220° C. at 8° C. per minute) indicates that no yield of product is formed.

FIG. 3 is the GLC profile for the reaction product of Example I(B).

Figure 1:
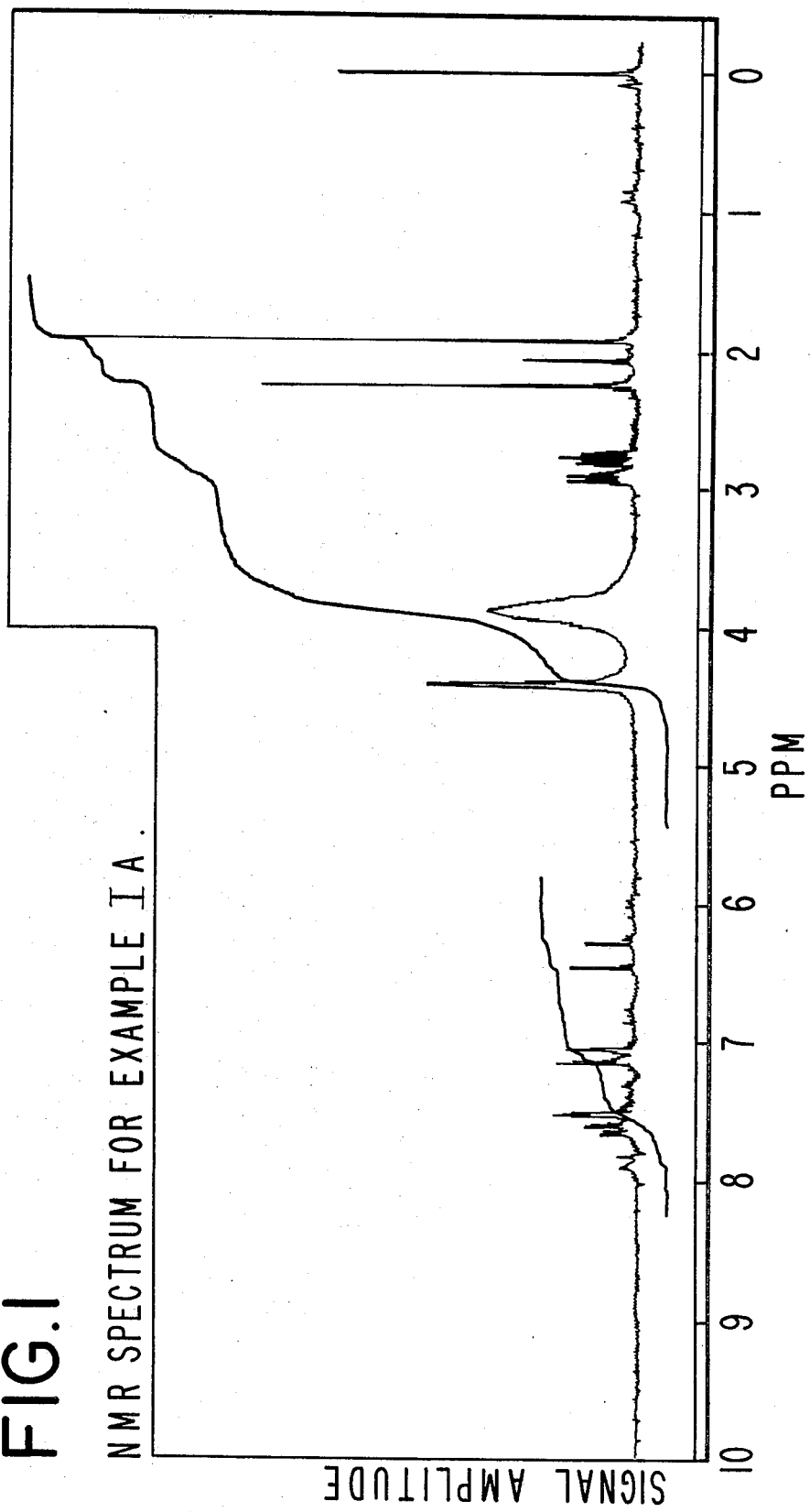
FIG. 1 is the NMR spectrum for the compound having the structure.

FIG. 1 is the NMR spectrum for paraacetoxy cinnamic acid produced according to Example I(A).

FIG. 2 is the infra-red spectrum for the paraacetoxy cinnamic acid having the structure:

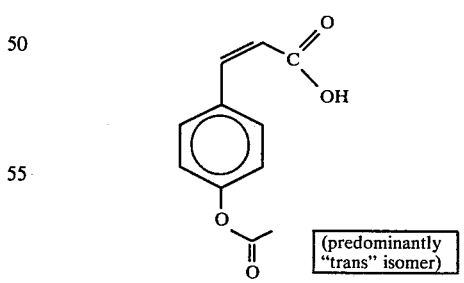

produced according to Example I(A).

EXAMPLE II
ATTEMPTED PREPARATION OF FOOD GRADE PARAVINYL PHENOL UNSUCCESSFUL

Reaction:

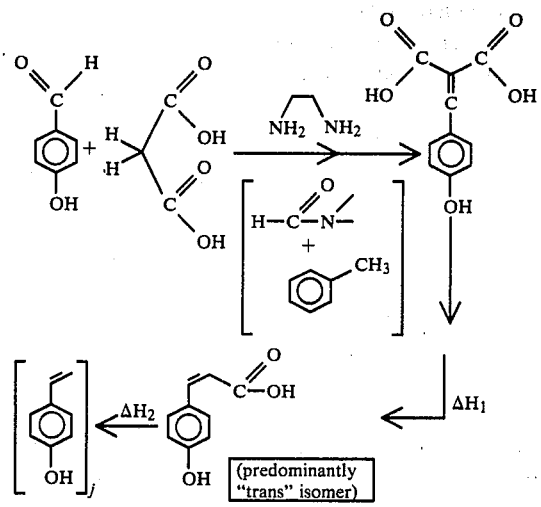

Into a 5 liter reaction flask equipped with electric stirrer, heating mantle, thermometer, Bidwell trap and reflux condenser as well as thermal watch are placed 244 grams (2.0 moles) of parahydroxybenzaldehyde; 223 grams (2.15 moles) of malonic acid; 5 grams of ethylenediamine; 806 ml dimethyl formamide and 604 ml toluene.

The reaction mass is heated to 99° C. and the reaction mass is refluxed for a period of 3 hours at a temperature of 117° C. (the thermal watch is set for 118° C.) The total amount of water removed into the Bidwell trap is 30 ml.

The reaction apparatus is then set up for recovery of the toluene solvent. As the toluene solvent is stripped off, it is replaced by an equal quantity of dimethyl formamide through the addition funnel.

The reaction mass is heated to a temperature in the range of 135°–143° C. while the toluene is stripped off and while dimethyl formamide is added. The toluene is stripped off over a period of 1 hour during which period of time 650 ml dimethyl formamide is added. At the end of the addition of the dimethyl formamide, the reaction mass is heated to 143° C. and maintained at 143° C. for a period of 1 hour during which all of the carbon dioxide is released and the reaction product is now paravinyl phenol mixed with dimethyl formamide.

The dimethyl formamide is stripped off in vacuo at 36°–41° vapor temperature and 5 mm Hg pressure.

At the end of the dimethyl formamide distillation, the reaction product is cooled to room temperature and 500 ml more dimethyl formamide is added together with 1 liter water to decrease the viscosity of the reaction mass.

The resulting reaction product is heavy "residue-like". The reaction mass is transferred to a 10 liter separatory funnel and 2 liters of water and 1 liter of toluene are added. Attempted extractions with water followed by drying using sodium sulfate, followed by distillation in a 2" stone packed column yielding the following fractions:

| Fraction Number | Vapor Temp. (°C.) | Liquid Temp. (°C.) | Head Vac. mm Hg Pressure | Weight of Fraction |
|---|---|---|---|---|
| 1 | 22/30 | 25/65 | 8.0/2.0 | — |
| 2 | 82 | 103 | 1.0 | 8.22 |

-continued

| Fraction Number | Vapor Temp. (°C.) | Liquid Temp. (°C.) | Head Vac. mm Hg Pressure | Weight of Fraction |
|---|---|---|---|---|
| 3 | 85 | 100 | 1.0 | 10.40 |
| 4 | 87 | 102 | 1.0 | 20.17 |
| 5 | 87 | 113 | 1.0 | 23.57 |
| 6 | 75 | 165 | 1.0 | 6.21 | yielded as inseparable mixture of toluene and paravinyl phenol unusable for food grade paravinyl phenol and unusable for flavors.

FIG. 4 represents the GLC profile for the paravinyl phenol produced thusly.

FIG. 5 is the NMR spectrum for the paravinyl phenol produced thusly.

In FIG. 4, peak 1 represents the paravinyl phenol

It should be noted that fraction 4 shows the 50-50 toluene as solvent.

EXAMPLE III

PREPARATION OF PARAACETOXY STYRENE (EXAMPLE III(A))

Reaction:

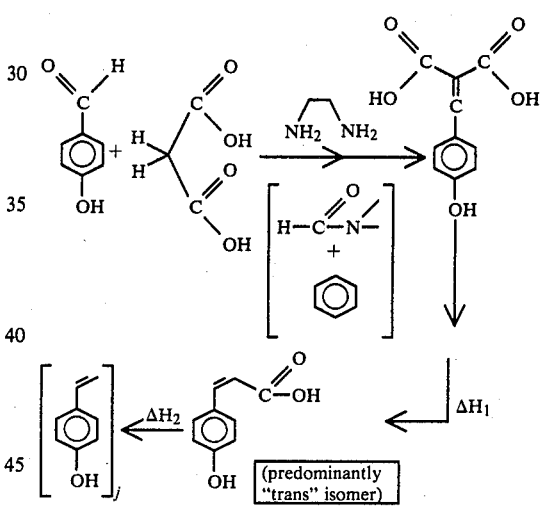

(EXAMPLE III(B))

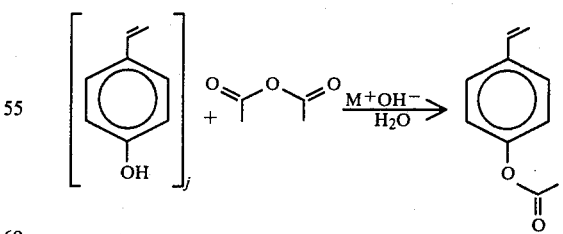

EXAMPLE III(A)

Preparation of Impure Paravinyl Phenol

Into a 5 liter reaction flask equipped with electric stirrer, heating mantle, thermometer, Bidwell trap, reflux condenser and thermal watch is placed 244 grams of parahydroxybenzaldehyde (2.0 moles); 223 grams (2.15 moles) malonic acid; 5 grams ethylenediamine; 806 ml dimethyl formamide and 604 ml cyclohexane.

The reaction mass is heated to 99° C. and refluxing commences. The thermal watch is set for 82° C. and the reaction mass is refluxed at a temperature of 80°-82° C. for a period of 4.5 hours during which time 82 ml of water is azeotroped off. At the end of the 4.5 hour period, the water ceases to be azeotroped off and the cyclohexane is stripped off through the Bidwell trap.

While the cyclohexane is stripped off, it is replaced with a equal volume of dimethyl formamide through the addition funnel. After 20 minutes at a pot temperature of 90° C., all of the cyclohexane is stripped off and all of the dimethyl formamide has been added to the reaction mixture.

The reaction mass is then heated to 115°-118° C. for decarboxylation. The decarboxylation takes place over a period of 8.0 hours. At the end of the 8 hour period during which time the reaction mass was heated at 114°-118° C., all of the carbon dioxide is removed.

The reaction apparatus is then set up for dimethyl formamide recovery and the dimethyl formamide is recovered at 70° C. under vacuum. At the end of the dimethyl formamide stripping, the reaction mass is cooled and poured into 2 liters of saturated sodium chloride solution. The reaction mass is then extracted with two 1 liter portions of cyclohexane. One liter of water is then added to the two phase system. The resulting product separated into three layers; a cyclohexane layer, a middle water layer and a lower residue layer. One liter of ethylacetate was added to the heavy residue layer for extraction purposes along with one liter of saturated sodium chloride solution. The ethylacetate and cyclohexane extracts are combined and the combined ethylacetate-cyclohexane extracts are then stripped on a Buchi evaporator yielding 29 grams of impure crystal. The impure crystal is then distilled on a 2" splash column yielding the following fractions:

| Fraction Number | Vapor Temp. (°C.) | Liquid Temp. (°C.) | Head Vac. mm Hg Pressure | Weight of Fraction |
|---|---|---|---|---|
| 1 | 25/37 | 53/24 | 1.0/1.0 | 42.6 |
| 2 | 52 | 76 | 1.0 | 32.7 |
| 3 | 74 | 86 | 1.0 | 29.5 |
| 4 | 82 | 93 | 1.0 | 48.7 |
| 5 | 80 | 125 | 1.0 | 26.4 |

FIG. 6A represents the GLC profile (conditions: SE-30 column, 10'×½" programmed at 100°-220° C. at 8° C. per minute) for the cyclohexane layer.

FIG. 6B represents the GLC profile for the heavy oil layer.

FIG. 6C represents the GLC profile for the heavy oil layer after extraction with ethylacetate.

FIG. 6D represents the GLC profile for the combined ethylacetate and cyclohexane extracts.

FIG. 6E represents the GLC profile for the crude reaction product.

FIG. 6F represents the GLC profile for fraction 3 of the distillation product resulting from the fractional distillation above.

FIG. 6G represents the GLC profile for fraction 4 of the distillation product for the distillation of the reaction product as above.

FIG. 6H represents the GLC profile for fraction 5 of the distillation product for the distillation set forth above.

EXAMPLE III(B)

Into a liter reaction flask equipped with cooling bath, electric stirrer, thermometer and addition funnel as well as separatory funnel for work-up is added a solution of 15 grams of sodium hydroxide in 800 ml water. Over a 10 minute period, 26 grams of the paravinyl phenol prepared in Example III(A) is added to the caustic solution.

Over a 10 minute period, 54 grams of acetic anhydride is added to the reaction mass while maintaining same at a temperature of between 20°-25° C. After addition of the acetic anhydride is complete, the reaction mass is stirred at a temperature of between 20°-25° C. for a 10 minute period.

The reaction mass is then poured into the separatory funnel and extracted with three 200 ml volumes of diethylether. The diethylether extracts are then combined and washed with one 100 ml portion of 10% sodium hydroxide followed by one 100 ml portion of water. The resulting organic layer is then dried over anhydrous sodium sulfate, filtered, stripped of solvent on a Buchi evaporator and distilled yielding the following fractions:

| Fraction Number | Vapor Temp. (°C.) | Liquid Temp. (°C.) | Head Vac. mm Hg. Pressure |
|---|---|---|---|
| 1 | 101/104 | 108/108 | 50/30 |
| 2 | 106 | 112 | 50/30 |
| 3 | 100 | 138 | 50/30 |
| 4 | 85 | 160 | 50/30 |

FIG. 7 is the NMR spectrum for paraacetoxy styrene having the structure:

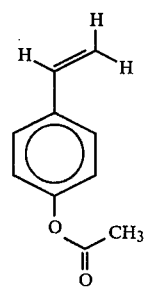

of which fraction 2 consists.

EXAMPLE IV

PREPARATION OF PARAVINYL PHENOL (EXAMPLE IV(A))

Reaction:

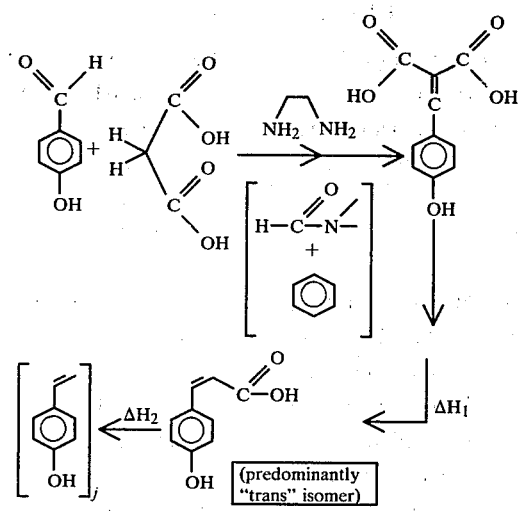

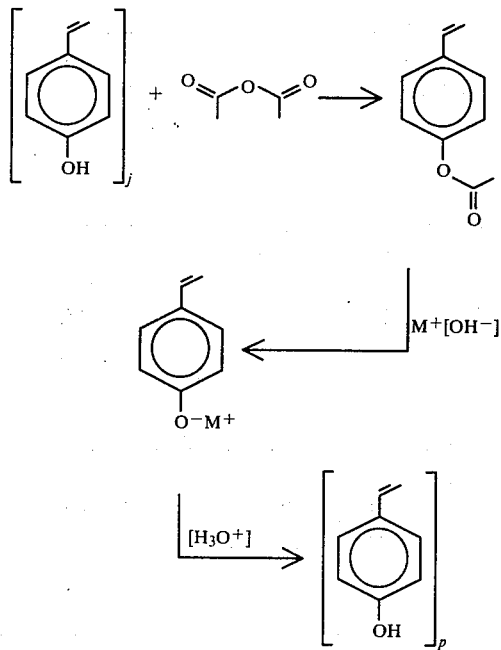

(EXAMPLE IV(B) and Example IV(C))

EXAMPLE IV(A)

Into a 5 liter reaction flask equipped with heating mantle, electric stirrer, thermometer, reflux condenser, Bidwell trap addition funnel and thermal watch is placed 244 grams of parahydroxybenzaldehyde; 223 grams of malonic acid, 5 grams of ethylenediamine; 806 ml dimethyl formamide and 644 ml of cyclohexane.

The reaction mass is heated to reflux and refluxed at 80° C. for a period of 15 hours after which time 85 ml of water is removed into the Bidwell trap.

At this point in time, cyclohexane is removed through the Bidwell trap but no dimethyl formamide is added while the cyclohexane is being stripped off. After the cyclohexane is stripped off, the reaction mass is heated to 115° C. for decarboxylation and while maintaining the reaction mass at 115° C. for a period of 11 hours, the reaction product is decarboxylated to yield impure paravinyl phenol.

The reaction mass is cooled and poured into a 20 liter separatory funnel and 10 liters of water (4 volumes) is then added to the reaction mass. The reaction mass is then extracted with three 1.5 liter volumes of ethylacetate. The organic layers are combined and washed with one 2 liter portion of saturated sodium chloride solution and then dried over anhydrous sodium sulfate, filtered and stripped of ethylacetate on a Buchi evaporator using 25 mm Hg. vacuum.

After the ethylacetate is stripped, the reaction mass (impure paravinyl phenol) is used for the next step.

EXAMPLE IV(B)

Into a 5 liter reaction flask equipped with cooling bath, reflux condenser, electric stirrer, and thermometer is placed 122 grams of crude paravinyl phenol separated according to Example IV(A) and a solution of 45 grams of sodium hydroxide in 2400 grams of water. The reaction mass is cooled to 20°–25° C. and over a period of one hour 416 grams of acetic anhydride is added to the reaction mass while maintaining the pot temperature at 20°–25° C. At the end of the addition of the acetic anhydride, the reaction mass is stirred for a period of 3.5 hours at 22°–23° C.

The reaction mass is then poured into a 5 liter separatory funnel and extracted with three 1 liter diethylether portions. The diethylether extracts are then combined and washed with one 1 liter portion of 10% aqueous sodium hydroxide. The extracts are then washed with one 1 liter portion of saturated sodium chloride solution, dried over anhydrous sodium sulfate, stripped of ether on a Buchi evaporator and distilled using a 2" stone packed column yielding the following fractions:

| Fraction Number | Vapor Temp. (°C.) | Liquid Temp. (°C.) | Head Vac. mm Hg. Pressure | Weight of Fraction |
|---|---|---|---|---|
| 1 | 74/75 | 89/98 | 2 | 12.7 |
| 2 | 82 | 103 | 2 | 21.8 |
| 3 | 85 | 112 | 2 | 54.1 |
| 4 | 84 | 143 | 2 | 22.1 |
| 5 | 125 | 220 | 2 | 18.1 |

EXAMPLE IV(C)

Into a 2 liter reaction flask equipped with cooling bath, heating mantle, electric stirrer, thermometer and addition funnel is placed 129 grams of paraacetoxy styrene produced according to Example IV(B) and a solution of 112 grams of potassium hydroxide in 1120 ml water. The resulting reaction mass is heated to 35°–40° C. until all the paraacetoxy styrene is consumed by the base. This takes approximately 45 minutes. The reaction mass is then cooled to 20°–25° C. and over a period of 0.5 hours, enough 10% aqueous acetic acid is added to the reaction mass to bring the pH to 6 (630 ml 10% aqueous acetic acid added). At this point, 75 grams of crystals precipitate. The crystals are washed with 150 ml water and air dried to yield food grade, substantially pure paravinyl phenol.

FIG. 8 is the infra-red spectrum for the food grade paravinyl phenol.

EXAMPLE V
(EXAMPLE V(A))
Reaction:

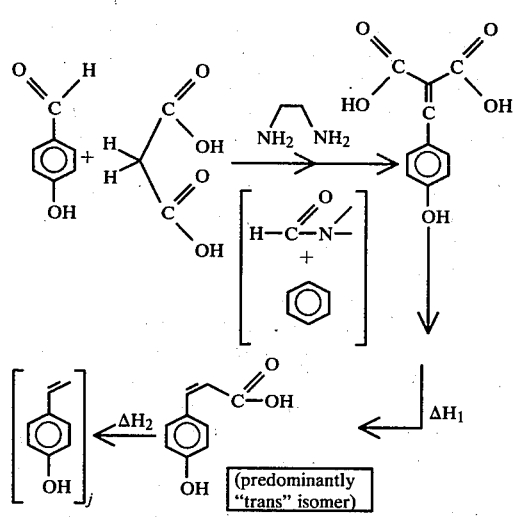

(EXAMPLE V(B) and EXAMPLE V(C))

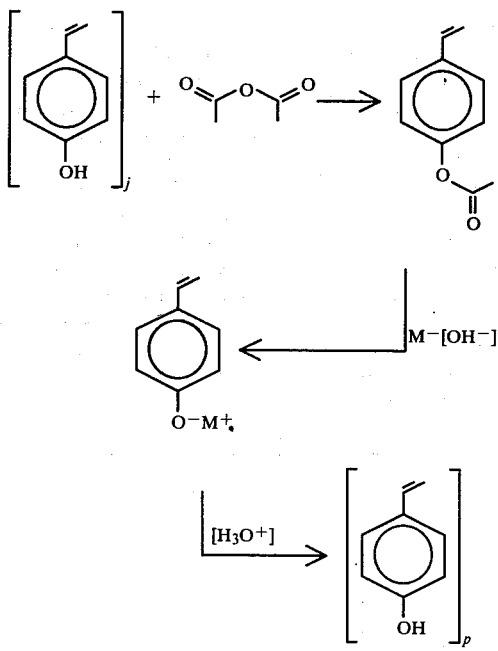

EXAMPLE V(A)

Into a 5 liter reaction flask equipped with heating mantle, electric stirrer, thermometer, reflux condenser, Bidwell trap, addition funnel and thermal watch is placed 244 grams parahydroxybenzaldehyde, 223 grams malonic acid, 5 grams ethylenediamine, 806 ml dimethyl formamide and 644 ml of cyclohexane.

The reaction mass is heated to reflux and refluxed for a period of 7.5 hours at 78°–79° C. during which time 83 ml water is evolved into the Bidwell trap.

The reaction mass is heated to reflux and cyclohexane is removed through the Bidwell trap while adding an equal amount of dimethyl formamide through the addition funnel. After all of the cyclohexane is removed and all of the dimethyl formamide is in, the reaction mixture is heated from 95° C. up to 115° C. for decarboxylation using the thermal watch and primal bubbler to monitor $CO_2$ evolution. The decarboxylation takes 12 hours and the temperature of decarboxylation is 115° C.

After completion of the decarboxylation, the reaction mass is cooled to room temperature and poured into a 20 liter separatory funnel and 10 liters of water (4 volumes) is added. The contents of the separatory funnel is stirred and the mass is extracted with three 1.5 liter volumes of ethylacetate. All the organic layers are combined and washed with one 2 liter portion of saturated sodium chloride solution. The resulting organic material is dried over anhydrous sodium sulfate filtered and stripped of ethylacetate on Buchi evaporator using 25 mm Hg pressure.

The resulting product is cooled and used as such in the following Example V(B).

EXAMPLE V(B)

Into a 3 liter reaction flask equipped with electric stirrer, thermometer, addition funnel, cooling bath and reflux condenser is placed 228 grams of the impure paravinyl phenol produced according to Example V(A) and a solution of 45 grams of sodium hydroxide in 2400 ml water. While maintaining the reaction temperature at 23°–24° C. over a one hour period, 400 ml acetic anhydride is added to the reaction mass. At the end of the addition of the acetic anhydride, the reaction mass is stirred for a period of 2.5 hours at 23°–24° C. at which time GLC monitoring (Carbowax: 2'×⅛" column programmed at 100°–220° C. at 8° C. per minute) indicates that the reaction is complete.

The reaction mass is poured into a 5 liter separatory funnel and extracted with three 1 liter volume portions of diethylether. The extracts are combined and washed with one 1 liter portion of 10% sodium hydroxide followed by one 1 liter portion of water. The organic material is then dried over anhydrous sodium sulfate filtered and stripped of ether on a Buchi evaporator. The reaction product is then distilled on a micro column yielding the following fractions:

| Fraction Number | Vapor Temp. (°C.) | Liquid Temp. (°C.) | Head Vac. mm Hg. Pressure | Weight of Fraction | GC Data; Product |
|---|---|---|---|---|---|
| 1 | 90 | 98 | 1.0 | 28.8 | 86% |
| 2 | 90 | 102 | 1.0 | 27.6 | |
| 3 | 85 | 100 | 1.0 | 46.1 | |
| 4 | 95 | 122 | 1.0 | 11.7 | 90% |
| 5 | 86 | 140 | 1.0 | 0.8 | |

The product produced in paraacetoxy styrene.

EXAMPLE V(C)

Into a 1 liter beaker equipped with stirring bar and hot plate is placed 50 grams of the paraacetoxy styrene produced according to Example V(B) and a KOH solution consisting of 43.4 grams of KOH in 430 grams of water. The reaction mass is stirred for one hour and heated to 40° C. to dissolve the paraacetoxy styrene into solution. After the paraacetoxy styrene is dissolved in the KOH solution, the reaction mass is cooled to room temperature. 10% acetic acid solution (20 grams acetic acid in 180 grams water) until the pH is approximately 6. The amount of acetic acid used is 210 grams.

Paravinyl phenol precipitates at this point (yield: 28 grams). The paravinyl phenol is filtered and washed with water and then air dried yielding a food grade material useful for food flavoring.

FIG. 9 sets forth the GLC profile for the resultant paravinyl phenol.

FIG. 10 sets forth the NMR spectrum for the resultant paravinyl phenol.

EXAMPLE VI

PREPARATION OF PARAVINYL PHENOL (EXAMPLE VI(A))

Reaction:

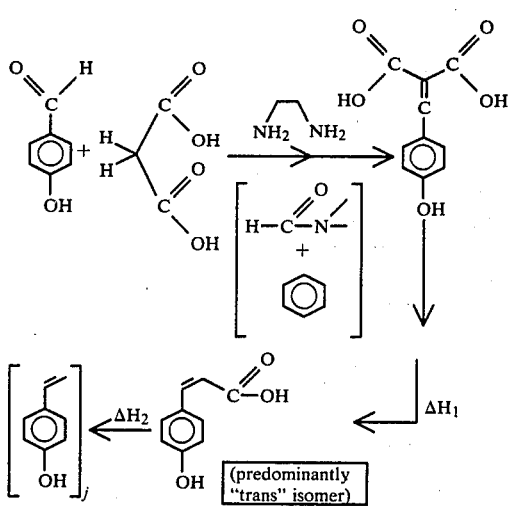

(EXAMPLE VI(B) and EXAMPLE VI(C))

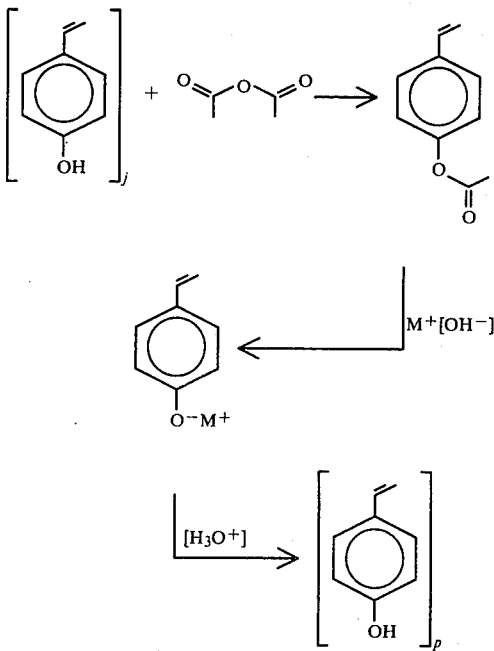

EXAMPLE VI(A)

Into a 12 liter reaction flask equipped with air stirrer, thermometer, heating mantle, large Bidwell trap and large bubble condenser are placed 3000 grams cyclohexane; 1500 grams parahydroxybenzaldehyde; 1338 grams malonic acid; 2000 grams dimethyl formamide and 30 grams of ethylenediamine.

The reaction mass is heated at 76°–78° C. for a period of 14 hours at the end of which time 338 grams of water is recovered in the Bidwell trap.

At the end of the reaction to form the carboxylic acid, the cyclohexane is recovered at 80°–89° C. The reaction mass is then heated to 115° C. to decarboxylate the reaction product and the decarboxylation continues at 115° C. for a period of 5 hours.

At the end of the decarboxylation, the reaction mass is transferred to a 5 gallon separatory funnel and washed with 4 volumes of water is added followed by 3 liters of ethylacetate. The ethylacetate extracts are combined and washed with one liter of water followed by 1.5 liters of saturated sodium chloride solution. The resultant material is dried over anhydrous sodium sulfate and distilled on a 1" splash column at 32° C. vapor temperature and 50° C. liquid temperature at 35 mm vacuum.

EXAMPLE VI(B)

Into a 5 liter reaction flask equipped with cooling bath, electric stirrer, thermometer, addition funnel and five liter separatory funnel for work-up is placed 456 grams of the impure paravinyl phenol produced according to Example VI(A) and 45 grams of sodium hydroxide in 2400 ml water. Over a period of 1 hour while maintaining the reaction mass at 20°–25° C., 400 ml (3.92 moles) of acetic anhydride is added to the reaction mass. After addition is complete, the reaction mass is poured into a 5 liter separatory funnel; extracted with three 1 liter volumes of diethylether followed by one 1 liter portion of 10% sodium hydroxide followed by one 1 liter portion of water. The organic layer is then dried over anhydrous sodium sulfate and distilled to yield the following fractions:

| Fraction Number | Vapor Temp. (°C.) | Liquid Temp. (°C.) | Head Vac. mm Hg. Pressure |
|---|---|---|---|
| 1 | 91 | 100 | 2.0 |
| 2 | 94 | 121 | 2.0 |
| 3 | 99 | 170 | 2.0 |

FIG. 11 sets for the the GLC profile for the resultant paraacetoxy styrene having the structure:

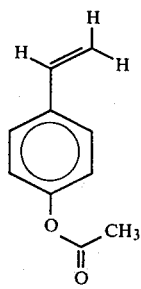

EXAMPLE VI(C)

Into a 5 liter reaction flask equipped with heating mantle, cooling bath, electric stirrer, thermometer, addition funnel, and reflux condenser is placed 243 grams of the paraacetoxy styrene produced according to Example VIB and a KOH solution consisting of 211 grams of KOH and 2110 grams of water. The reaction mass is heated to 38°-40° C. and maintained at 38°-40° C. until all of the paraacetoxy styrene is consumed. The reaction mass is then cooled to room temperature (21° C.) and over a one hour period a solution of 10% acetic acid (1250 ml) is added whereby the reaction mass is brought to a pH of 6. At this point, 230 grams of paravinyl phenol precipitates and this paravinyl phenol is of food grade quality.

FIG. 12 sets forth the infra-red spectrum for the resultant paravinyl phenol.

EXAMPLE VII

PREPARATION OF PARAACETOXY STYRENE

Reaction:

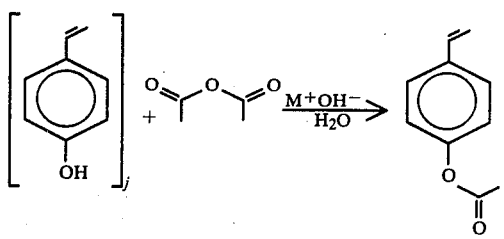

Into a 5 liter reaction flask equipped with cooling bath, electric stirrer, thermometer, addition funnel, and five liter separatory funnel for work-up is placed a sodium hydroxide solution consisting of 23 grams of sodium hydroxide in 1200 ml water followed by 242 grams of paravinyl phenol prepared according to Example VI(A). The reaction mass is cooled to 22°-23° C. and over a 45 minute period, 221 ml of acetic anhydride is added to the reaction mass while maintaining its temperature at 20°-25° C. throughout the addition.

After the addition of the acetic anhydride is complete, the reaction mass is poured into a 5 liter separatory funnel for work-up. The reaction mass is then extracted with three 600 ml portions of diethylether and the ether extracts are combined and washed with one 500 ml portion of 10% sodium hydroxide solution followed by one 500 ml portion of water. The organic material is then dried over anhydrous sodium sulfate, filtered and stripped of solvent atmospherically. The reaction mass is then distilled on a 1" splash column yielding the following fractions:

| Fraction Number | Vapor Temp. (°C.) | Liquid Temp. (°C.) | Head Vac. mm Hg. Pressure | Weight of Fraction |
|---|---|---|---|---|
| 1 | 70/110 | 120/140 | 4.0 | 6.5 |
| 2 | 110 | 145 | 4.0 | 10.8 |
| 3 | 105 | 200 | 4.0 | 11.4 |

FIG. 13A is the GLC profile (conditions: Carbowax 10'×⅛" column programmed at 100°-220° C. at 8° C. per minute) for fraction 1 of the foregoing distillation and contains paravinyl phenol and paraacetoxy styrene.

FIG. 13B is the GLC profile for fraction 2 of the foregoing distillation and contains paravinyl phenol and paraacetoxy styrene.

FIG. 13C represents the GLC profile for fraction 3 of the foregoing distillation and contains paravinyl phenol and paraacetoxy styrene.

FIG. 13D represents the GLC profile for the residue of the foregoing distillation.

In FIG. 13A, the peak indicated with reference numeral "2" is the peak for paraacetoxy styrene having the structure:

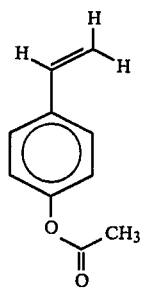

In FIG. 13A, the peak indicated by reference numeral "3" is the peak for paravinyl phenol having the structure:

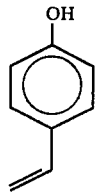

What is claimed is:

1. In the process for preparing paravinyl phenol in food grade form of food grade quality comprising the steps, in sequential order, of:
   (i) intimately admixing malonic acid and parahydroxybenzaldehyde in the presence of ethylenediamine, dimethyl formamide and an inert solvent while heating the reaction mixture at reflux thereby forming a first reaction product located within a first reaction mass;
   (ii) removing water of reaction from the first reaction mass while simultaneously heating the said first reaction mass at a refluxing temperature;
   (iii) removing the solvent from the first reaction mass;
   (iv) decarboxylating the resulting first reaction product by heating the reaction product to a temperature in the range of 115°-120° C. thereby forming a second reaction product;
   (v) dissolving in water and extracting with a lower alkyl ester the reaction product; and
   (vi) stripping the solvent from the reaction product to yield a second reaction mass which comprises paravinyl phenol;

the improvement of which consists essentially of the additional steps of:
   (vii) admixing acetic anhydride and dilute aqueous base with the resulting second reaction products to form paraacetoxy styrene from the paravinyl phenol contained in said second reaction mass;
   (viii) fractionally distilling the paraacetoxy styrene from the second reaction mass;

(ix) hydrolyzing the paraacetoxy styrene by mixing therewith a strong base to produce the alkali metal salt of paravinyl phenol having the structure:

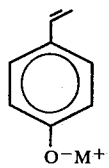

wherein M represents an alkali metal selected from the group consisting of sodium and potassium thereby forming a third reaction mass;

(x) adding dilute aqueous acid to the resulting third reaction mass whereby crystalline paravinyl phenol precipitates; and (xi) separating the resulting precipitate from the resulting solution, the solvent being used in conjunction with the step of intimately admixing malonic acid and parahydroxy benzaldehyde consisting essentially of cyclohexane.

2. The process of claim 1 wherein the temperature which is the refluxing temperature step (ii) is from about 75° C. up to about 80° C.

3. The process of claim 1 wherein the weight ratio of cyclohexane:parahydroxy benzaldehyde is from about 3:1 up to about 1.2:1 and the weight ratio of parahydroxy benzaldehyde:malonic acid is from about 1.5:1 down to about 1:1 and the weight ratio of parahydroxy benzaldehyde:dimethyl formamide is from about 1:4 up to about 1:1 and the weight ratio of ethylene diamine catalyst:parahydroxy benzaldehyde is from about 5:1000 up to about 5:100.

4. The process of claim 2 wherein the weight ratio of cyclohexane:parahydroxy benzaldehyde is from about 3:1 up to about 1.2:1, the weight ratio of parahydroxy benzaldehyde:malonic acid is from about 1.5:1 down to 1:1, the weight ratio of parahydroxy benzaldehyde:dimethyl formamide is from about 1:4 up to about 1:1, and the weight ratio of ethylene diamine catalyst:parahydroxy benzaldehyde is from about 5:1000 up to about 5:100.

5. The process of claim 1 wherein while the cyclohexane solvent is being stripped off, the volume of solvent in the reaction mass in step (iii) is maintained constant by adding back thereto an equivalent volume of dimethyl formamide.

6. The process of claim 2 wherein step (iii) while the cyclohexane solvent is being stripped off, the volume of the solvent in the reaction mass is maintained constant by adding back thereto an equivalent volume of dimethyl formamide.

7. The process of claim 3 wherein in step (iii), while the cyclohexane solvent is being stripped off, the volume of the solvent in the reaction mass is maintained constant by adding back thereto an equivalent volume of dimethyl formamide.

8. The process of claim 1 wherein the improvement also consists of the additional step (xii) of drying the paravinyl phenol crystals resulting from the practice of step (xi).

9. The process of claim 1 wherein the improvement also consists of the additional step (xii) following step (xi) of drying the paravinyl phenol crystals resulting from the practice of step (xi).

* * * * *